US010350277B2

(12) United States Patent
Schuchman et al.

(10) Patent No.: US 10,350,277 B2
(45) Date of Patent: Jul. 16, 2019

(54) CERAMIDASE AND CELL DIFFERENTIATION

(75) Inventors: Edward H. Schuchman, Haworth, NJ (US); Calogera M. Simonaro, Haworth, NJ (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 1286 days.

(21) Appl. No.: 14/343,150

(22) PCT Filed: Sep. 7, 2012

(86) PCT No.: PCT/US2012/054316
§ 371 (c)(1),
(2), (4) Date: Jun. 6, 2014

(87) PCT Pub. No.: WO2013/036875
PCT Pub. Date: Mar. 14, 2013

(65) Prior Publication Data
US 2014/0287015 A1 Sep. 25, 2014

Related U.S. Application Data

(60) Provisional application No. 61/531,917, filed on Sep. 7, 2011.

(51) Int. Cl.
| | | |
|---|---|---|
| C12N 5/077 | (2010.01) | |
| A61K 38/50 | (2006.01) | |
| A61K 35/32 | (2015.01) | |
| A61K 38/18 | (2006.01) | |

(52) U.S. Cl.
CPC .............. *A61K 38/50* (2013.01); *A61K 35/32* (2013.01); *A61K 38/1841* (2013.01); *C12N 5/0655* (2013.01); *C12Y 305/01023* (2013.01); *C12N 2501/73* (2013.01); *C12N 2506/1353* (2013.01)

(58) Field of Classification Search
CPC .................................................. C12N 5/0655
See application file for complete search history.

(56) References Cited

U.S. PATENT DOCUMENTS

| | | |
|---|---|---|
| 3,966,555 A | 6/1976 | Arnaud et al. |
| 3,972,777 A | 8/1976 | Yamada et al. |
| 4,450,238 A | 5/1984 | Vitobello et al. |
| 4,837,028 A | 6/1989 | Allen |
| 5,019,369 A | 5/1991 | Presant et al. |
| 5,382,524 A | 1/1995 | Desnick et al. |
| 5,401,650 A | 3/1995 | Desnick et al. |
| 5,433,946 A | 7/1995 | Allen, Jr. et al. |
| 5,580,757 A | 12/1996 | Desnick et al. |
| 5,688,766 A | 11/1997 | Revis |
| 6,066,626 A | 5/2000 | Yew et al. |
| 6,258,581 B1 | 7/2001 | Okino et al. |
| 6,350,768 B1 | 2/2002 | Bohme et al. |
| 6,379,699 B1 | 4/2002 | Virtanen et al. |
| 6,489,117 B2 | 12/2002 | Okino et al. |
| 6,537,785 B1 | 3/2003 | Canfield |
| 6,541,218 B1 | 4/2003 | Schuchman et al. |
| 6,730,297 B1 | 5/2004 | Davidson et al. |
| 6,767,741 B1 | 7/2004 | Epstein et al. |
| RE38,689 E | 1/2005 | Okino et al. |
| 6,858,383 B2 | 2/2005 | Sabbadini |
| 6,881,546 B2 | 4/2005 | Sabbadini |
| 6,884,435 B1 | 4/2005 | O'Hagan et al. |
| 7,018,628 B1 | 3/2006 | Sarkis et al. |
| 7,232,670 B2 | 6/2007 | D'Azzo et al. |
| 7,273,756 B2 | 9/2007 | Adkisson et al. |
| 7,927,587 B2 | 4/2011 | Blazer et al. |
| 8,017,394 B2 | 9/2011 | Adkisson, IV et al. |
| 2003/0087868 A1 | 5/2003 | Yew et al. |
| 2003/0157086 A1 | 8/2003 | Tilly et al. |
| 2003/0206911 A1 | 11/2003 | Muzykantov et al. |
| 2003/0211604 A1 | 11/2003 | Brown |
| 2003/0215435 A1 | 11/2003 | Berent |
| 2004/0029779 A1 | 2/2004 | Zhu |
| 2004/0039046 A1 | 2/2004 | Deigner |
| 2004/0172665 A1 | 9/2004 | Reuser et al. |
| 2004/0204379 A1 | 10/2004 | Cheng et al. |
| 2004/0242539 A1 | 12/2004 | Fan et al. |
| 2004/0247603 A1 | 12/2004 | Sabbadini |
| 2004/0248262 A1 | 12/2004 | Koeberl et al. |

(Continued)

FOREIGN PATENT DOCUMENTS

| | | |
|---|---|---|
| CN | 1688316 A | 10/2005 |
| CN | 101479288 A | 7/2009 |

(Continued)

OTHER PUBLICATIONS

Gilbert et al. (2006, Arthritis Res. and Therapy, vol. 8(4), pp. 1-11).*
Okino et al., 2003, JBC, vol. 278(32), pp. 22948-23953.*
Gilbert et al., 2008, Arthritis and Rheumatism, vol. 58(1), pp. 209-220.*
Sabatini et al., 2000, Biochem Biophys Res. Comm., vol. 267, pp. 438-444.*
Supplementary European Search Report and European Search Opinion for European Application 14775400.6 (dated Jun. 27, 2016).
English Translation and Office Action for Chinese Application No. 201280037341.5 (dated Jul. 26, 2016).
Restriction Requirement for U.S. Appl. No. 14/776,442 (dated Aug. 26, 2016).
Achord et al., "Human beta-Glucuronidase: In Vivo Clearance and In vitro Uptake by a Glycoprotein Recognition System on Reticuloendothelial Cells," *Cell* 15(1):269-78 (1978).

(Continued)

*Primary Examiner* — Thaian N Ton
*Assistant Examiner* — David A. Montanari
(74) *Attorney, Agent, or Firm* — Pepper Hamilton LLP

(57) ABSTRACT

The present invention relates to methods of producing chondrocytes, improving the phenotype of a chondrocyte population, promoting chondrogenesis, maintaining a cell population in a differentiated state or increasing the number of cells of a population in a differentiated state, producing a population of differentiated cells, and treating certain diseases or disorders. Each of these methods involves treating a cell population with, and/or culturing a cell population in, a ceramidase.

11 Claims, 8 Drawing Sheets

(56) References Cited

U.S. PATENT DOCUMENTS

| | | |
|---|---|---|
| 2005/0026823 A1 | 2/2005 | Zankel et al. |
| 2005/0112640 A1 | 5/2005 | Davidson et al. |
| 2006/0154252 A1 | 7/2006 | Marguerie et al. |
| 2007/0009500 A1 | 1/2007 | Blazar et al. |
| 2007/0162992 A1 | 7/2007 | Burns |
| 2007/0184439 A1 | 8/2007 | Guilford et al. |
| 2007/0292949 A1 | 12/2007 | Duguay et al. |
| 2008/0045470 A1 | 2/2008 | Bielawska et al. |
| 2008/0057590 A1 | 3/2008 | Urdea et al. |
| 2008/0199450 A1 | 8/2008 | Schuchman et al. |
| 2008/0248481 A1 | 10/2008 | Rapko et al. |
| 2008/0292618 A1 | 11/2008 | Weisbart |
| 2010/0068302 A1 | 3/2010 | Ramirez De Molina et al. |
| 2010/0160253 A1 | 6/2010 | Coombe et al. |
| 2010/0285139 A1 | 11/2010 | Gulbins |
| 2011/0091439 A1 | 4/2011 | Bernard et al. |
| 2011/0091442 A1 | 4/2011 | Boyd et al. |
| 2014/0287015 A1 | 9/2014 | Schuchman et al. |
| 2015/0132368 A1 | 5/2015 | Muro Galindo et al. |

FOREIGN PATENT DOCUMENTS

| | | |
|---|---|---|
| CN | 102368905 A | 3/2012 |
| JP | 2002/542195 A | 12/2002 |
| JP | 2003/516122 A | 5/2003 |
| JP | 2004/083465 A | 3/2004 |
| WO | WO 90/11353 | 10/1990 |
| WO | WO 00/62780 | 10/2000 |
| WO | WO 01/26678 A1 | 4/2001 |
| WO | WO 02/087510 A2 | 11/2002 |
| WO | WO 2004/057031 A2 | 7/2004 |
| WO | WO 2006/007560 A2 | 1/2006 |
| WO | WO 2006/113289 A2 | 10/2006 |
| WO | WO 2007/089734 A2 | 8/2007 |
| WO | WO 2007/095688 A1 | 8/2007 |
| WO | 2007/117996 A2 | 10/2007 |
| WO | WO 2007/136635 A1 | 11/2007 |
| WO | 2008086296 A2 | 7/2008 |
| WO | 2008148063 A1 | 12/2008 |
| WO | 2009155936 A1 | 12/2009 |
| WO | WO 2010/127355 A1 | 11/2010 |
| WO | WO 2011/025996 A2 | 3/2011 |
| WO | 2011066352 A1 | 6/2011 |
| WO | WO 2012/051415 A2 | 4/2012 |
| WO | WO 2012/154794 A2 | 11/2012 |
| WO | WO 2012/177778 A1 | 12/2012 |
| WO | WO 2013/036875 A1 | 3/2013 |
| WO | WO 2013/101276 A2 | 7/2013 |
| WO | WO 2013/181530 A1 | 12/2013 |
| WO | WO 2014/160390 A1 | 10/2014 |

OTHER PUBLICATIONS

Agnieszka et al., "Prenatal Diagnosis-Principles of Diagnostic Procedures and Genetic Counseling," *Folia Histochemica et Cytobiologica* 45:11-16 (2007).

Almenar-Queralt et al., "Apical Topography and Modulation of ICAM-1 Expression on Activated Endothelium," *Am. J. Pathol.* 147(5): 1278-88 (1995).

Auclair et al., "Intra-Articular Enzyme Administration for Joint Disease in Feline Mucopolysaccharidosis VI: Enzyme Dose and Interval," *Pediatr. Res.* 59(4):538-43 (2006).

Barton et al., "Therapeutic Response to Intravenous Infusions of Glucocerebrosidase in a Patient with Gaucher Disease, " *Proc. Natl. Acad. Sci. USA* 87(5): 1913-6 (1990).

Bawab et al., "Ceramidases in the Regulation of Ceramide Levels and Function," *Subcellular Biochemistry*, vol. 36, Chapter 10, Phospholipid Metabolism in Apoptosis, Quinn et al., Eds., Kluwer Academic/Plenum Publishers, New York (2002).

Bazian, "Ultra Drug Orphan Drugs for Lysosomal Storage Disorders: A Guideline Comparison and Survey of International Current Practice," 1-70 (2009).

Becker et al., "Acid Sphingomyelinase Inhibitors Normalize Pulmonary Ceramide and Inflammation in Cystic Fibrosis," *Am. J. Respir. Cell Mol. Biol.* 42:716-24 (2010).

Berlin and Oliver, "Surface Functions During Mitosis," *J. Cell. Biol.* 85:660-671 (1980).

Bernardo et al., "Purification, Characterization, and Biosynthesis of Human Acid Ceramidase," *J. Biol. Chem.* 270(19):11098-11102 (1995).

Bernstein et al., "Fabry Disease: Six Gene Rearrangements and an Exonic Point Mutation in the alpha-Galactosidase Gene," *J. Clin. Invest.* 83(4):1390-1399 (1989).

Beutler et al., "Purification and Properties of Human alpha-Galactosidases," *J. Biol. Chem.* 247(22):7195-7200 (1972).

Beutler, E., "Gaucher Disease: New Molecular Approaches to Diagnosis and Treatment," *Science* 256:794-799 (1992).

Bhowmick et al., "Effect of Flow on Endothelial Endocytosis of Nanocarriers Targeted to ICAM-1," *J. Controlled Release* 157(3):485-492 (2012).

Bielicki et al., "Advantages of Using Same Species Enzyme for Replacement Therapy in a Feline Model of Mucopolysaccharidosis Type VI," *The Journal of Biological Chemistry* 274(51)36335-36343 (1999).

Bielicki et al., "Recombinant Canine alpha-L-Fucosidase: Expression, Purification, and Characterization," *Mol. Gen. Metabolism* 69:24-32 (2000).

Bishop et al., "Affinity Purification of alpha-Galactosidase A From Human Spleen, Placenta, and Plasma With Elimination of Pyrogen Contamination. Properties of the Purified Splenic Enzyme Compared to other Forms," *J. Biol. Chem.* 256(3):1307-1316 (1981).

Bishop et al., "Enzyme Therapy XX: Further Evidence for the Differential In Vivo Fate of Human Splenic and Plasma . . . ", in *Lysosomes and Lysosomal Storage Diseases*, Eds. Callahan et al. Raven Press; 381-94 (1981).

Bishop et al., "Human alpha-Galactosidase A: Nucleotide Sequence of a cDNA Clone Encoding the Mature Enzyme," *Proc. Natl. Acad. Sci.* 83(13):4859-4863 (1986).

Bishop et al., "Human α-Galactosidase: Characterization and Eukaryotic Expression of the Full-Length cDNA and Structural Organization of the Gene" in *Lipid Storage Disorders*, Eds. Salvayre et al. Plenum Publishing Corp 809-822 (1988).

Bishop et al., "Molecular Cloning and Nucleotide Sequencing of a Complementary DNA Encoding Human Alpha Galactosidase A," *Am. J. Hum. Genetics* 37 (4 Suppl):A144 (1985).

Bishop et al., "Purification and Characterization of Human alpha-Galactosidase Isozymes: Comparison of Tissue and Plasma Forms and Evaluation of Purification Methods," *Birth Defects Original Article Series*; XVI(1): 17-32 (1980).

Bishop et al., "Structural Organization of the Human alpha-Galactosidase A Gene: Further Evidence for the Absence of a 3' Untranslated Region," *Proc. Natl. Acad. Sci.* 85(11):3903-3907 (1988).

Bodas et al., "Critical Modifier Role of Membrane-Cystic Fibrosis Transmembrane Conductance Regulator-Dependent Ceramide Signaling in Lung Injury and Emphysema," *J. Immunol.* 186:602-613 (2011).

Bonten et al., "Targeting Macrophages With Baculovirus-Produced Lysosomal Enzymes: Implications for Enzyme Replacement Therapy of the Glycoprotein Storage Disorder Galactosialidosis," *FASEB J.* 18(9):971-3 (Epub 2004).

Boose et al., "Conditional Intercellular Cohesion in a *Dictyostelium discoideum* Mutant Which is Temperature Sensitive for Correct Processing of Asparagine-Linked Oligosaccharides," *Glycobiology* 1(3):295-305 (1991).

Brady et al., "Enzyme Replacement Therapy: Conception, Chaos and Culmination." *Phil. Trans. R. Soc. London B Biol. Sci.* 358(1433):915-9 (2003).

Brady et al., "Modifying Exogenous Glucocerebrosidase for Effective Replacement Therapy in Gaucher Disease," *J. Inherit. Dis.* 17(4):510-9 (1994).

Brady et al., "Replacement Therapy for Inherited Enzyme Deficiency. Use of Purified Ceramidetrihexosidase in Fabry's Disease." *N. Engl. J. Med.* 289(1):9-14 (1973).

(56) References Cited

OTHER PUBLICATIONS

Broun et al., "Catalytic Plasticity of Fatty Acid Modification Enzymes Underlying Chemical Diversity of Plant Lipids," *Science* 282:1315-1317 (1998).
Cabrera-Salazar et al., "Gene Therapy for the Lysosomal Storage Disorders," *Curr. Opin. Mol. Ther.* 4(4):349-58 (2002).
Calhoun et al., "Fabry Disease: Isolation of a cDNA Clone Encoding Human Alpha-Galactosidase A," *Proc. Natl. Acad. Sci.* 82(21):7364-7368 (1985).
Callahan et al., "Alpha-N-Acetylgalactosaminidase: Isolation, Properties and Distribution of the Human Enzyme," *Biochemical Med.* 7(3):424-431 (1973).
Chavez et al., "Acid Ceramidase Overexpression Prevents the Inhibitory Effects of Saturated Fatty Acids in Insulin Signaling," *J. Biol. Chem.* 280(20):20148-53 (2006).
Chelikani et al., "Diversity of Structures and Properties Among Catalases," *Cell Mol. Life Sci.* 61:192-208 (2004).
Chica et al., "Semi-Rational Approaches to Engineering Enzyme Activity: Combining the Benefits of Directed Evolution and Rational Design," *Curr. Opi. Biotechnol.* 16:378-384 (2005).
Christofidou-Solomidou et al., "Vascular Immunotargeting of Glucose Oxidase to the Endothelial Antigens Induces Distinct Forms of Oxidant Acute Lung Injury: Targeting to Thrombomodulin, but not to PECAM-1, Causes Pulmonary Thrombosis and Neutrophil Transmigration," *Am. J. Pathol.* 160(3):1155-69 (2002).
Conner and Schmid, "Regulated Portals of Entry Into the Cell," *Nature* 422:37-44 (2003).
Coppola et al., "Construction of. Baculovirus Derivatives that Overproduce Human α-Galactosidase A," *J. Cell. Biochem. Suppl.* Abstract No. K306 13D:227-347 (1989).
D'Azzo, "Gene Transfer Strategies for Correction of Lysosomal Storage Disorders," *Acta Haematol.* 110(2-3):71-85 (2003).
Daly & Sands, "Gene Therapy for Lysosomal Storage Diseases," *Expert Opin. Invest. Drugs* 7(10):1673-82 (1998).
Dean et al., "Studies on Human Liver Alpha-Galactosidases. II. Purification and Enzymatic Properties of Alpha-Galactosidase B (alpha-N-acetylgalactosaminidase)," *J. Biol. Chem.* 254(20):10001-10005 (1979).
Dean et al., "The Identification of Alpha-Galactosidase B From Human Liver as an Alpha-N-Acetylgalactosaminidase," *Biochem. Biophys. Res. Commun.* 77(4):1411-1417 (1977).
Desnick et al., "Enzyme Replacement and Enhancement Therapies: Lessons From Lysosomal Disorders," *Nature Rev. Genet.*; 3(12):954-66 (2002).
Desnick et al., "Enzyme Therapy in Fabry Disease: Differential In Vivo Plasma Clearance and Metabolic Effectiveness of Plasma and Splenic Alpha-Galactosidase A Isozymes," *Proc. Natl. Acad. Sci. USA* 76(10):5326-5330 (1979).
Desnick et al., "Enzyme therapy XVII: Metabolic and Immunologic Evaluation of Alpha-Galactosidase A Replacement in Fabry Disease," *Birth Defects Original Article Series*; XVI(1):393-413 (1980).
Desnick et al., "Fabry Disease: a-Galactosidase Deficiency; Schindler Disease: α-N-Acetylgalactosaminidase Deficiency." in *The Metabolic Basis of Inherited Disease*, eds. Scriver et al. McGraw Hill, NY; 70: 1751-96 (1989).
Desnick et al., "Fabry Disease: Molecular Diagnosis of Hemizygotes and Heterozygotes," *Enzyme* 38(1-4):54-64 (1987).
Desnick et al., "Schindler Disease: An Inherited Neuroaxonal Dystrophy Due to alpha-N-Acetylgalactosaminidase Deficiency," *J. Inher. Metab. Dis.* 13:549-559 (1990).
Devos et al., "Practical Limits of Function Prediction," *Proteins: Structure, Function, and Genetics* 41:98-107 (2000).
Dhami et al., "Mannose 6-phosphate Receptor-Mediated Uptake is Defective in Acid Sphingomyelinase-Deficient Macrophages: Implications for Niemann-Pick Disease Enzyme Replacement Therapy," *J. Biol. Chem.* 279(2): 1526-32 (2004).
Diamond et al., "Binding of the Integrin Mac-1 (CD11b/CD18) to the Third Immunoglobulin-Like Domain of ICAM-1 (CD54) and its Regulation by Glycosylation," *Cell* 65:961-71 (1991).

Eliyahu et al., "Acid Ceramidase Improves the Quality of Oocytes and Embryos and the Outcome of in Vitro Fertilization," *FASEB J.* 24:1229-38 (2010).
Eliyahu et al., "Acid Ceramidase is a Novel Factor Required for Early Embryo Survival," Abstract Presented in Mar. 2007.
Eliyahu et al., "Acid Ceramidase is a Novel Factor Required for Early Embryo Survival," *FASEB J.* 21:1403-09 (May 2007).
Eliyahu et al., "Anti-TNF-Alpha Therapy Enhances the Effects of Enzyme Replacement Therapy in Rats with Mucopolysaccharidosis Type VI," *PLOS ONE* 6(8):e22447 (2011).
Eliyahu et al., "Identification of Cystatin SA as a Novel Inhibitor of Acid Ceramidase," *J. Biol. Chem.* 286(41):35624-33 (2011).
Ellinwood et al., "Gene Therapy for Lysosomal Storage Diseases: The Lessons and Promise of Animal Models," *J. Gene Med.* 6(5):481-506 (2004).
Eng et al., "Safety and Efficacy of Recombinant Human alpha-Galactosidase A Replacement Therapy in Fabry's Disease," *N. Eng. J. Med.* 345(1):9-16 (2001).
Estruch et al., "Non-Viral, Integrin-Mediated Gene Transfer into Fibroblasts From Patients With Lysosomal Storage Diseases." in *J. Gene Med.* 3(5):488-97 (2001).
European Patent Application No. 08727393.4, Supplementary European Search Report (dated Sep. 9, 2010).
European Patent Office Communication and Examination Report for European Patent Application No. 08727393.4 (dated Dec. 4, 2014).
Extended European Search Report for European Patent Application No. 12803458.4 (dated Mar. 20, 2015).
Farkas et al., "The Recycling of Apolipoprotein E and its Amino-Terminal 22 kDa Fragment: Evidence of Multiple Redundant Pathways," *J. Lipid Res.* 45:1546-1554 (2004).
Fawcett, "Surface Specializations of Absorbing Cells," *J. Histochem. Cytochem.* 13(2):75-91 (1965).
Ferlinz et al., "Functional Characterization of the N-Glycosylation Sites of Human Acid Sphingomyelinase by Site-Directed Mutagenesis," *Eur. J. Biochem.* 243:511-517 (1997).
Ferlinz et al., "Occurrence of Two Molecular Forms of Human Acid Sphingomyelinase," *Biochem. J.* 301:855-862 (1994).
First Office Action and English Translation for Chinese Patent Application No. 201280037341.5 (dated Dec. 3, 2014).
Fox et al., "Circulating Sphingolipid Biomarkers in Models of Type 1 Diabetes," *Journal of Lipid Research*, 30 pp., retrieved from www.jlr.org on Jan. 6, 2011.
Friedman et al., "A Comparison of the Pharmacological Properties of Carbohydrate Remodeled Recombinant and Placental-Derived beta-Glucocerebrosidase: Implications for Clinical Efficacy in Treatment of Gaucher Disease," *Blood* 93(9):2807-16 (1999).
Furbish et al., "Uptake and Distribution of Placental Glucocerebrosidase in Rat Hepatic Cells and Effects of Sequential Deglycosylation," *Biochem. Biophys. Acta.* 673(4):425-34 (1981).
Gao et al., "Delivery of a Retroviral Vector Expressing Human beta-Glucuronidase to the Liver and Spleen Decreases Lysosomal Storage in Mucopolysaccharidosis VII Mice," *Mol. Ther.* 2(2):233-44 (2000).
Garman & Garboczi, "The Molecular Defect Leading to Fabry Disease: Structure of Human α-Galactosidase," *J. Mol. Biol.* 337(2):319-335 (2004).
Garman et al., "The 1.9 A Structure of α-N-Acetylgalactosaminidase", *Structure* 10(3):425-434 (2002).
Gilbert et al., "Sphingomyelinase Decreases Type II Collagen Expression in Bovine Articular Cartilage Chondrocytes via the ERK Signaling Pathway," *Arthritis & Rheumatism* 58(1):209-220 (2008).
Gole et al. "Plasma Proteins Modified by Tyrosine Nitration in Acute Respiratory Distress Syndrome," *Am. J. Physiol. Lung Cell Mol. Physiol.* 278(5):L961-967 (2000).
Grabowski et al., "Enzyme Therapy for Lysosomal Storage Disease: Principles, Practice, and Prospects." *Annu. Rev. Genomics Hum. Genet.*; 4:403-36 (2003).
Grabowski et al., "Enzyme Therapy in Type 1 Gaucher Disease: Comparative Efficacy of Mannose-Terminated Glucocerebrosidase from Natural and Recombinant Sources," *Ann. Intern. Med.* 122:33-39 (1995).

(56) References Cited

OTHER PUBLICATIONS

Grassme et al., "CTFR-Dependent Susceptibility of the Cystic Fibrosis-Host to Pseudomonas aeruginosa," *Int. J. Med. Microbiol.* 300:578-583 (2010).
Hanzopoulos & Calhoun, "Expression of the Human alpha-Galactosidase A in *Escherichia coli* K-12," *Gene (Amst.)* 57(2-3):159-169 (1987).
Harmatz et al., "Enzyme Replacement Therapy in Mucopolysaccharidosis VI (Maroteaux-Lamy Syndrome)," *J. Pediatr.* 144:574-80 (2004).
Hasholt & Sorenson, "Lysosomal Alpha-Galactosidase in Endothelial Cell Cultures Established From a Fabry Hemizygous and Normal Umbilical Veins," *Human Genet.* 72(1):72-76 (1986).
Haskins et al., "Bone Marrow Transplantation Therapy for Metabolic Disease: Animal Models as Predictors of Success and In Utero Approaches," *Bone Marrow Transplant* 18(Suppl. 3): S25-S27 (1996).
He et al., "Characterization of Human Acid Sphingomyelinase pPurified From the Media of Overexpressing Chinese Hamster Ovary Cells," *Biochim. Biophys. Acta.* 1432(2):251-64 (1999).
He et al., "Deregulation of Sphingolipid Metabolism in Alzheimer's Disease," *Neurobiology of Aging* 31(3):398-408 (2010).
He et al., "Purification and Characterization of Recombinant, Human Acid Ceramidase. Catalytic Reactions and Interactions With Acid Sphingomyelinase," *J. Biol. Chem.* 278(35):32978-86 (2003).
Hers et al., "Alpha-Glucosidase Deficiency in Generalized Glycogenstorage Gisease (Pompe's Gisease)," *Biochem. J.* 86:11-16 (Jan. 1963).
Hlavacek et al., "Steric Effects on Multivalent Ligand-Receptor Binding: Exclusion of Ligand Sites by Bound Cell Surface Receptors," *Biophysical J.* 76:3031-3043 (1999).
Hoogerbrugge et al., "Effect of Bone Marrow Transplantation on Enzyme Levels and Clinical Course in the Neurologically Affected Twitcher Mouse," *J. Clin. Invest.* 81(6): 1790-4 (Jun. 1988).
Huang et al., "A Comparison of the Signal Pathways Between the TNFalpha-and Oridonin-Induced Murine L929 Fibrosarcoma Cell Death," *Acta Med. Okayama* 59(6):261-70 (2005).
Huang et al., "Elevation of the Level and Activity of Acid Ceramidase in Alzheimer's Disease Brain," *Europ. J. Neurosci.* 20:3489-3497 (2004).
International Preliminary Report on Patentability for PCT/US2008/050418 (dated Jul. 16, 2009).
International Search Report and Written Opinion for PCT/US2008/050418 (dated Oct. 8, 2008).
International Search Report and Written Opinion for International Application No. PCT/US05/23529 (dated Aug. 2, 2006).
International Search Report and Written Opinion for International Application No. PCT/US2014/026481 (dated Aug. 11, 2014).
International Search Report and Written Opinion for PCT Application No. PCT/US2012/043369 (dated Aug. 31, 2012).
International Search Report and Written Opinion for PCT/US10/33422 (dated Jun. 29, 2010).
International Search Report and Written Opinion for PCT/US11/56147 (dated Apr. 26, 2012).
International Search Report and Written Opinion for PCT/US13/043608 (dated Oct. 21, 2013).
International Search Report and Written Opinion for PCT/US2012/031847 (dated Jul. 22, 2013).
Ioannou et al., "Overexpression and Characterization of Human alpha-Galactosidase," in *Inborn Errors of Metabolism, 5th International Congress*, Abstract No. OC4.3, Pacific Grove, CA (Jun. 1-5, 1990).
Ioannou et al., "Fabry Disease: Preclinical Studies Demonstrate the Effectiveness of alpha-Galactosidase A Replacement in Enzyme-Deficient Mice," *Am J. Hum. Genet.* 68:14-25 (2001).
Isemura et al., "Characterization and Amino Acid Sequence of New Acidic Cysteine Proteinase Inhibitor (Cystatin SA) Structurally Closely Related to Cystatin S, From Human Whole Saliva," *J. Biochem.* 102(4):693-704 (1987).
Jan et al., "Sindbis Virus Entry Into Cells Triggers Apoptosis by Activating Sphingomyelinase,"*J. Virol.* 74(14):6425-32 (2000).
Jin et al., "Ex Vivo Gene Therapy Using Bone Marrow-Derived Cells: Combined Effects of Intracerebral and Intravenous Transplantation in a Mouse Model of Niemann-Pick Disease," *Mol. Ther.* 8(6):876-85 (2003).
Jin et al., "Intracerebral Transplantation of Mesenchymal Stem Cells Into Acid Sphingomyelinase-Deficient Mice Delays the Onset of Neurological Abnormalities and Extends Their Life Span." *J. Clin. Invest.* 109(9):1183-91 (2002).
Kakkis et al., "Long-Term and High-Dose Trials of Enzyme Replacement Therapy in the Canine Model of Mucopolysaccharidosis I," *Biochem. Mol. Med.* 58:156-67 (1996).
Kaplan et al., "Phosphohexosyl Components of a Lysosomal Enzyme are Recognized by Pinocytosis Receptors on Human Fibroblasts," *Proc. Natl. Acad. Sci. USA*; 74(5):2026-30 (1977).
Kato et al., "Cystatin SA, A Cysteine Proteinase Inhibitor, Induces Interferon-Gamma Expression in CD4-Positive T Cells," *Biol. Chem.* 385(5):419-22 (2004).
Kishida et al., "Docosahexaenoic Acid Enrichment Can Reduce L929 Cell Necrosis Induced by Tumor Necrosis Factor," *Biochim. Biophys. Acta* 1761:454-62 (2006).
Kisselev, L., "Polypeptide Release Factors in Prokaryotes and Eurkaryotes: Same Function, Different Structure," *Structure* 10:8-9 (2002).
Klabunde et al., "Mechanism of Fe(III)—Zn(II) Purple Acid Phosphatase Based on Crystal Structures," *J. Mol. Biol.* 259:737-748 (1996).
Kölzer et al., "Functional Characterization of the Postulated Intramolecular Sphingolipid Activator Protein Domain of Human Acid Sphingomyelinase," *Biol. Chem.* 385:1193-1195 (2004).
Kornfeld et al., "Lysosomal Enzyme Targeting," *Biochem. Soc. Trans.* 18(3):367-74 (1990).
Kornfeld et al., "Trafficking of Lysosomal Enzymes," *FASEB J.* 1(6):462-468 (1987).
Kornfeld et al., "Steps in the Phosphorylation of the High Mannose Oligosaccharides of Lysosomal Enzymes," *CIBA Found. Symp.*; (92):138-56 (1982).
Kornreich et al., "Alpha-Galactosidase A Gene Rearrangements Causing Fabry Disease. Identification of Short Direct Repeats at Breakpoints in an Alu-Rich Gene," *J. Biol. Chem.* 265(16): 9319-9326 (1990).
Kornreich et al., "Nucleotide Sequence of the Human Alpha-Galactosidase A Gene," *Nuc. Acids. Res.* 17(8):3301-3302 (1989).
Kozower et al., "Immunotargeting of Catalase to the Pulmonary Endothelium Alleviates Oxidative Stress and Reduces Acute Lung Transplantation Injury," *Nat. Biotechnol.* 21(4):392-8 (2003).
Krivit et al., "State of the Art Review. Bone Marrow Transplantation Treatment for Storage Diseases.Keystone," *Bone Marrow Transplant* 10(Suppl. 1): 87-96 (1992).
Kusiak et al., "Purification and Properties of the Two Major Isozymes of Alpha-Galactosidase From Human Placenta," *J. Biol. Chem.* 253(1): 184-190 (1978).
Lansmann et al., "Human Acid Sphingomyelinase—Assignment of the Disulfide Bond Pattern," *Eur. J. Biochem.* 270:1076-1088 (2003).
Le Roy et al., "Clathrin-and non-Clathrin Mediated Endocytic Regulation of Cell Signalling," *Nature* 6:112-126 (2005).
Lebowitz et al., "Glycosylation-Independent Targeting Enhances Enzyme Delivery to Lysosomes and Decreases Storage in Mucopolysaccharidosis Type VII Mice," *Proc. Natl. Acad. Sci. USA* 101(9):3083-8 (2004).
Leimig et al., "Functional Amelioration of Murine Galactosialidosis by Genetically Modified Bone Marrow Hematopoietic Progenitor Cells," *Blood* 99(9)3169-78 (2002).
Lemansky et al., "Synthesis and Processing of Alpha-Galactosidase A in Human Fibroblasts. Evidence for Different Mutations in Fabry Disease," *J. Biol. Chem.* 262(5):2062-2065 (1987).
Li et al., "Insertional Mutagenesis of the Mouse Acid Ceramidase Gene Leads to Early Embryonic Lethality in Homozygotes and Progressive Lipid Storage Disease in Heterozygotes," *Genomics* 79(2):218-24 (2002).
Lin et al., "*Caenorhabditis elegans* Contains Two Distinct Acid Sphingomyelinases," *J. Biol. Chem.* 273(23): 14374-14379 (1998).
Liu et al., "Acid Ceramidase Upregulation in Prostate Cancer: Role in Tumor Development and Implications for Therapy," *Expert Opinions in Therapeutic Targets* 13(12):1449-1458 (2009).

(56) References Cited

OTHER PUBLICATIONS

Malatack et al., "The Status of Hematopoietic Stem Cell Transplantation in Lysosomal Storage Disease," *Pediatr. Neurol.* 29(5):391-403 (2003).
Mao et al., "Cloning and Characterization of a Novel Human Ceramidase," *J. Biol. Chem.* 276(28):26577-26588 (2001).
Medline Plus Online Dictionary; Definition for "embryo".
Meikle et al., "Prevalence of Lysosomal Storage Disorders." *JAMA* 281(3): 249-54 (1999).
Mielke et al., "Alterations of the Sphingolipid Pathway in Alzheimer's Disease: New Biomarkers and Treatment Targets?," *Neuromol. Med.* 12:331-340 (2010).
Mintzer et al., "A Novel High-Throughput Screening Format to Identify Inhibitors of Secreted Acid Sphingomye linase," *J. Biomol. Screen* 10(3):225-34 (2005).
Miranda et al., "Biochemical, Pathological, and Clinical Response to Transplantation of Normal Bone Marrow Cells Into Acid Sphingomyelinase-Deficient Mice," *Transplantation* 65(7):884-92 (1998).
Miranda et al., "Bone Marrow Transplantation in Acid Sphingomyelinase-Deficient Mice: Engraftment and Cell Migration Into the Brain as a Function of Radiation, Age, and Phenotype," *Blood* 90(1):444-52 (1997).
Miranda et al., "Hematopoietic Stem Cell Gene Therapy Leads to Marked Visceral Organ Improvements and a Delayed Onset of Neurological Abnormalities in the Acid Sphingomyelinase Deficient Mouse Model of Niemann-Pick Disease," *Gene Ther.* 7:1768-76 (2000).
Miranda et al., "Infusion of Recombinant Human Acid Sphingomyelinase into Niemann-Pick Disease Mice Leads to Visceral, but Not Neurological, Correction of the Pathophysiology," *FASEB J.* 14:1988-95 (2000).
Mistry et al., "Therapeutic Delivery of Proteins to Macrophages: Implications for Treatment of Gaucher's Disease." *Lancet* 348(9041):1555-9 (1996).
Monick et al., "Cooperative Prosurvival Activity by ERK and AKT in Human Alveolar Macrophages is Dependent on High Levels of Acid Ceramidase Activity," *J. Immunol.* 173:123-35 (2004).
Morita et al., "Oocyte Apoptosis Is Suppressed by Disruption of the Acid Sphingomyelinase Gene or by Sphingosine-1-Phosphate Therapy," *Nat. Med.* 6(10):1109-14 (2000).
Murciano et al., "ICAM-Directed Vascular Immunotargeting of Antithrombotic Agents to the Endothelial Luminal Surface," *Blood* 101(10):3977-84 (2003).
Muro et al., "A Novel Endocytic Pathway Induced by Clustering Endothelial ICAM-1 or PECAM-1." *J. Cell Sci.* 116(Pt 8):1599-609 (2003).
Muro et al., "Endothelial Endocytic Pathways: Gates for Vascular Drug Delivery," *Curr. Vasc. Pharmacol.* 2(3):281-99 (2004).
Muro et al., "ICAM-1 Recycling in Endothelial Cells: A Novel Pathway for Sustained Intracellular Delivery and Prolonged Effects of Drugs," *Blood* 105(2):650-8 (2005).
Muro et al., "Slow Intracellular Trafficking of Catalase Nanoparticles Targeted to ICAM-1 Protects Endothelial Cells From Oxidative Stress," *Am. J. Physiol. Cell Physiol.* 285(5):C1339-47 (2003).
Murray, "Lectin-Specific Targeting of Lysosomal Enzymes to Reticuloendothelial Cells," *Meth. Enzymol.* 149:25-42 (1987).
Naslavsky et al., "Characterization of a Nonclathrin Endocytic Pathway: Membrane Cargo and Lipid Requirements," *Mol. Biol. Cell.* 15:3542-3552 (2004).
Newman et al., "The Biology of PECAM-1," *J. Clin. Invest.* 99(1):3-8 (1997).
Newrzella et al., "Functional Analysis of the Glycosylation of Murine Acid Sphingomyelinase," *J. Biol. Chem.* 271(50):32089-32095 (1996).
Newrzella et al., "Molecular Cloning of the Acid Sphingomyelinase of the Mouse and the Organization and Complete Nucleotide Sequence of the Gene," *Biol. Chem. Hoppe-Seyler* 373:1233-1238 (1992).
Nichols et al., "Endocytosis Without Clathrin Coats," *Trends in Cell Biol.* 11(10):406-412 (2001).
Office Action for Canadian Patent Application No. 2,674,849 (dated Feb. 4, 2015).
Okino et al., "The Reverse Activity of Human Acid Ceramidase," *J. Biol. Chem.* 278(32):29948-53 (2003).
Pandey et al., "Recent Advances in the Immunology of Ceramide," *Exp. Mol. Pathol.* 82:298-309 (2007) (E-pub Oct. 12, 2006).
Park & Schuchman, "Acid Ceramidase and Human Disease," *Biochim. Biophys. Acta* 1758:2133-38 (2006).
Park et al., "Ceramide, A Crucial Functional Lipid and Its Metabolic Regulation by Acid Ceramidase," *Food Science & Biotechnology* 19(4):859-864 (2010).
Partial Supplementary European Search Report for European Patent Application No. 12803458.4 (dated Dec. 1, 2014).
Pasqualotto et al., "Effect of Oxidative Stress in Follicular Fluid on the Outcome of Assisted Reproductive Procedures," *Fertility and Sterility* 81(4):973-76 (2004).
Patrizio et al., "Molecular Methods for Selection of the Ideal Oocyte," *Reproductive BioMedicine Online* 15(3):346-53 (2007).
Perez et al., "A Central Role for Ceramide in the Age-Related Acceleration of Apoptosis in the Female Germline," *FASEB J.* 19(7):860-2 (2005).
Pittis et al., "Acid Sphingomyelinase: Identification of Nine Novel Mutations Among Italian Niemann Pick Type B Patients and Characterization of In Vivo Functional In-Frame Start Codon," *Human Mutation, Mutation in Brief* #734 p. 1-7 (2004).
Ponting et al., "Acid sphingomyelinase possesses a domain homologous to its activator proteins: saposins B and D," *Protein Science* 3:359-361 (1994).
Pratico et al., "Localization of Distinct F2-Isoprostanes in Human Atherosclerotic Lesions." *J. Clin. Invest.* 100(8):2028-34 (1997).
Prince et al., "Lipoprotein Receptor Binding, Cellular Uptake, and Lysosomal Delivery of Fusions Between the Receptor-Associated Protein (RAP) and Alpha-L-Iduronidase or Acid Alpha-Glucosidase," *J. Biol. Chem.* 279(33):35037-46 (2004).
Qui et al., "Activation of Human acid Sphingomyelinase Through Modification or Deletion of C-Terminal Cysteine," *J. Biol. Chem.* 278(35):32744-32752 (2003).
Quinn et al., "A Genomic Clone Containing the Promoter for the Gene Encoding the Human Lysosomal Enzyme, Alpha-Galactosidase A," *Gene (Amst.).* 58(2-3): 177-188 (1987).
Quintern et al., "Acid Sphingomyelinase From Human Urine: Purification and Characterization," *Biochimica et Biophyszca Acta.* 922:323-336 (1987).
Rienzi et al., "Predictive Value of Oocyte Morphology in Human IVF: A Systematic Review of the Literature," *Hum. Reprod. Update* 17(1):33-45 (2011).
Romiti et al., "Neutral/Alkaline and Acid Ceramidase Activities Are Actively Released by Murine Endothelial Cells," *Biochem. Biophys. Res. Comm.* 275:746-51 (2000).
Roudebush et al, "Embryonic Platelet-Activating Factor: An Indicator of Embryo Viability," *Hum. Reprod.* 17(5):1306-10 (2002).
Rousseau et al., "Utilization of Membranous Lipid Substrates by Membranous Enzymes: Activation of the Latent Sphingomyelinase of Hen Erythrocyte Membrane," *Arch. Biochern. Biophys.* 244(2):838-45 (1986).
Sands et al., "Biodistribution, Kinetics, and Efficacy of Highly Phosphorylated and Non-Phosphorylated Beta-Glucuronidase in the Murine Model of Mucopolysaccharidosis VII," *J. Biol. Chem.* 276(46):43160-5 (2001).
Schindler et al., "Neuroaxonal Dystrophy Due to Lysosomal Alpha-N-Acetylgalactosaminidase Deficiency," *New Eng. J. Med.* 320(26):1735-1740 (1989).
Schram et al., "The Identity of Alpha-Galactosidase B From Human Liver," *Biochimica et Biophysica Acta.* 482(1):138-144 (1977).
Schuchman et al., "Human Acid Sphingomyelinase. Isolation, Nucleotide Sequence and Expression of the Full-Length and Alternatively Spliced cDNAs," *J. Biol. Chem.* 266(13):8531-8539 (1991).
Schuchman et al., "Pentosan Polysulfate: A Novel Therapy for the Mucopolysaccharidoses," *PLOS ONE* 8(1):e54459 (2013).
Scriver et al., Part 16: Lysosomal Disorders in: The Metabolic and Molecular Bases of Inherited Disease, 8th ed., McGraw-Hill (2000).

(56) References Cited

OTHER PUBLICATIONS

Second Office Action and English Translation for Chinese Patent Application No. 201280037341.5 (dated Nov. 3, 2015).
Seelan et al., "Human Acid Ceramidase is Overexpressed but Not Mutated in Prostate Cancer," *Genes Chromosomes & Cancer* 29:137 (2000).
Segui et al., "Stress-Induced Apoptosis Is Not Mediated by Endolysosomal Ceramide," *FASEB J.* 14:36-47 (2000).
Seli et al., "Noninvasive Metabolomic Profiling of Embryo Culture Media Using Proton Nuclear Magnetic Resonance Correlates With Reproductive Potential of Embryos in Women Undergoing in vitro fertilization," *Fertil. Steril.* 90:2183-89 (2008).
Sen et al., "Developments in Directed Evolution for Improving Enzyme Functions," *Appl. Biochem. Biotechnol.* 143:212-223 (2007).
Shtraizent et al., "Autoproteolytic Cleavage and Activation of Human Acid Ceramidase," *J. Biol. Chem.* 283(17):11253-9 (2008).
Simonaro et al., "Acid Ceramidase Improves the Chondrogenic Phenotype of Primary and Mesenchymal Stem Cell-Derived Chondrocytes: Implications for Cartilage Repair," *Osteoarthritis and Cartilage* 19(S1):S114-S115 (2011).
Simonaro et al., "Acid Ceramidase Maintains the Chondrogenic Phenotype of Expanded Primary Chondrocytes and Improves the Chondrogenic Differentiation of Bone Marrow-Derived Mesenchymal Stem Cells," *PLOS ONE* 8(4):e62715 (2013).
Simonaro et al., "Involvement of the Toll-like Receptor 4 Pathway and Use of TNF-alpha Antagonists for Treatment of the Mucopolysaccharidoses," *PNAS* 107(1)222-227 (2010).
Springer et al., "Traffic Signals for Lymphocyte Recirculation and Leukocyte Emigration: The Multistep Paradigm," *Cell* 76(2):301-14 (1994).
Stahl et al., "Evidence for Receptor-Mediated Binding of Glycoproteins, Glycoconjugates, and Lysosomal Glycosidases by Alveolar Macrophages," *Proc. Natl. Acad. Sci. USA* 75(3):1399-403 (1978).
Strelow et al., "Overexpression of Acid Ceramidase Protects from Tumor Necrosis Factor-Induced Cell Death," *J. Exp. Med.* 192(5):601-11 (2000).
Supplementary European Search Report for European Patent Application No. 13797635.3 (dated Jan. 22, 2016).
Sweeley et al., "Post-Translational Processing Reactions Involved in the Biosynthesis of Lysosomal Alpha-N-Acetylgalactosaminidase in Cultured Human Fibroblasts," *Archives of Biochem & Biophys.* 233(1):158-65 (1983).
Tang et al., "Identification of PECAM-1 in Solid Tumor Cells and Its Potential Involvement in Tumor Cell Adhesion to Endothelium," *J. Biol. Chem.* 268(30):22883-22894 (1993).
Taylor et al., "Decreased Lysosomal Storage in the Adult MPS VII Mouse Brain in the Vicinity of Grafts of Retroviral Vector-Corrected Fibroblasts Secreting High Levels of Beta-Glucuronidase," *Nature Med.* 3(7): 771-74 (1997).
Teichgraber et al., "Ceramide Accumulation Mediates Inflammation, Cell Death and Infection Susceptibility in Cystic Fibrosis," *Nat. Med.* 14(4):382-391 and Supplementary Information (2008).
Thon et al., "The Murine TRAIL Receptor Signals Caspase-Independent Cell Death Through Ceramide," *Experimental Cell Research* 312:3808-21 (2006).
Tsuji et al., "Molecular Cloning of a Full-Length cDNA for Human Alpha-N-Acetylgalactosaminidase (alpha-galactosidase B)," *Biochem. Biophys. Res. Commun.* 163(3):1498-1504 (1989).
Tsuji et al.,, "Signal Sequence and DNA-Mediated Expression of Human Lysosomal Alpha-Galactosidase A," *Eur. J. Biochem.* 165(2):275-280 (1987).
UniProt_D7BW40 (last modified Aug. 10, 2010).
UniProt_Q19784 ( last modified Sep. 11, 2007).
UniProt_Q8YUN7 (last modified Mar. 1, 2002).
Vanier et al., "Niemann-Pick Diseases," Handbook of Clinical Neurology, 113(3rd series):1717-1721 (2013).
Vellodi et al., "Bone Marrow Transplantation for Mucopolysaccharidosis Type I: Experience of Two British Centres," *Arch. Dis. Child.* 76(2):92-99 (1997).
Voraberger et al., "Cloning of the Human Gene for Intercellular Adhesion Molecule 1 and Analysis of its 5'-Regulatory Region," *J. Immunol.* 147(8):2777-2786 (1991).
Waheed et al., "Human Lysosomal Acid Phosphatase is Transported as a Transmembrane Protein to Lysosomes in Transfected Baby Hamster Kidney Cells," *EMBO J.* 7(8):2351-8 (1988).
Wang et al., "Human Alpha-N-Acetylgalactosaminidase-Molecular Cloning, Nucleotide Sequence, and Expression of a Full-Length cDNA. Homology with Human Alpha-Galactosidase A Suggests Evolution From a Common Ancestral Gene," *J. Biol. Chem.* 265(35):21859-21866 (1990).
Wang et al., "Molecular Genetics of PKU in Orientals," *Am J. Hum. Genet.* 45 (4 Suppl) A228 (1989).
Wang et al., "Schindler Disease Biochemical and Molecular Characterization of a New Neuroaxonal Dystrophy Due to Alpha-N. Acetylgalactosaminidase Deficiency," *Am. J. Hum. Genet.* 43 (3 Suppl):A99 (1988).
Wang et al., "Schindler Disease: The Molecular Lesion in the Alpha-N-Acetylgalactosaminidase Gene That Causes an Infantile Neuroaxonal Dystrophy," *J. Clin. Invest.* 86(5):1752-1756 (1990).
Weinreb et al., "Effectiveness of Enzyme Replacement Therapy in 1028 Patients with Type 1 Gaucher Disease After 2 to 5 Years of Treatment: A Report from the Gaucher Registry," *Am. J. Med.* 113:112-19 (2002).
Weinstein et al., "Primary Structure of Beta-Galactoside Alpha 2,6-Sialyltransferase. Conversion of Membrane-Bound Enzyme to Soluble Forms by Cleavage of the NH2-Terminal Signal Anchor," *J. Biol. Chem.* 262(36):17735-43 (1987).
Whisstock et al., "Prediction of Protein Function from Protein Sequence," *Q. Rev. Biophysics* 36(3):307-340 (2003).
Wiewrodt et al., "Size-Dependent Intracellular Immunotargeting of Therapeutic Cargoes Into Endothelial Cells," *Blood* 99(3):912-22 (2002).
Wishart et al., "A Single Mutation Converts a Novel Phosphotyrosine Binding Domain Into a Dual-Specificity Phosphatase," *J. Biol. Chem.* 270(45):26782-26785 (1995).
Witkowski et al., "Conversion of b-ketoacyl Synthase to a Malonyl Decarboxylase by Replacement of the Active Cysteine With Glutamine," *Biochemistry* 38:11643-11650 (1999).
Witsenburg et al., "Cumulative Live Birth Rates in Cohorts of Patients Treated With in Vitro Fertilization or Intracytoplasmic Sperm Injection," *Fertil. Steril.* 84(1):99-107 (2005).
Xu et al., "Golgi Alkaline Ceramidase Regulates Cell Proliferation and Survival by Controlling Levels of Sphingosine and SIP," *The FASEB Journal* 20:1813-25 (2006).
Yamauchi et al., "Molecular Cloning of Two Species of cDNAs for Human Alpha-N-Acetylgalactosaminidase and Expression in Mammalian Cells," *Biochem. Biophys. Res. Commun.* 170(1):231-37 (1990).
Yeyati et al., "Fluorescence-Based Selection of Retrovirally Transduced Cells in the Absence of a Marker Gene: Direct Selection of Transduced Type B Niemann-Pick Disease Cells and Evidence for Bystander Correction," *Hum. Gene Ther.* 6(8):975-83 (1995).
Young et al., "Sphingolipids: Regulators of Crosstalk Between Apoptosis and Autophagy," *J. Lipid. Res.* 54:5-19 (2013).
Zhang et al., "Delivery of Beta-Galactosidase to Mouse Brain via the Blood-Brain Barrier Transferrin Receptor," *J. Pharmacol. Exp. Ther.* 313(3):1075-81 (2005).
Zhu et al., "Dexamethasone-Mediated up-Regulation of the Mannose Receptor Improves the Delivery of Recombinant Glucocerebrosidase to Gaucher Macrophages." *J. Pharmacol. Exp. Ther.* 308(2):705-11 (2004).
Office Action for European Application No. 12803458.4 (dated Feb. 8, 2016).
English Translation and Notice of Reasons for Rejection of Japanese Patent Application No. 2015-515238 (dated Mar. 6, 2017).
Seikagaku, "Metabolism of Sphingolipids Centered on Ceramide," Biochemistry 83(6):495-505 (2011) (English abstract only).
English Translation and Fourth Office Action for Chinese Patent Application No. 201280037341.5 (dated Mar. 20, 2017).
English Translation and Second Office Action for Chinese Patent Application No. 201380031825.3 (dated Apr. 6, 2017).

(56) References Cited

OTHER PUBLICATIONS

Office Action for U.S. Appl. No. 14/776,442 (dated Dec. 9, 2016).
English Translation and Notice of Reasons for Rejection for Japanese Patent Application No. 2014-517125 (dated Dec. 12, 2016).
Extended European Search Report and Opinion for corresponding European Patent Application No. 12830086.0 (dated Jul. 13, 2015).
PCT International Search Report and Written Opinion for PCT/US2012/054316, filed Sep. 7, 2012 (dated Dec. 20, 2012).
Partial Supplementary European Search Report for corresponding European Patent Application No. 12830086.0 (dated Mar. 5, 2015).
Nejadnik et al., "Autologous Bone Marrow-Derived Mesenchymal Stem Cells Versus Autologous Chondrocyte Implantation: An Observational Cohort Study," The American Journal of Sports Medicine 38(6):1110-1116 (2010).
Ramsubir et al., "In Vivo Delivery of Human Acid Ceramidase Via Cord Blood Transplantation and Direct Injection of Lentivirus as Novel Treatment Approaches for Farber Disease," Molecular Genetics and Metabolism 95:133-141 (2008).
Walia et al., "Autologous Transplantation of Lentivector/Acid Ceramidase—Transduced Hematopoietic Cells in Nonhuman Primates," Human Gene Therapy 22:679-687 (2011).
MacRae et al., "Ceramide Inhibition of Chondrocyte Proliferation and Bone Growth is IGF-I Independent," Journal of Endocrinology 191:369-377 (2006).
Marquass et al., "Matrix-Associated Implantation of Predifferentiated Mesenchymal Stem Cells Versus Articular Chondrocytes: In Vivo Results of Cartilage Repair After 1 Year," The American Journal of Sports Medicine 39 (7):1401-1412 (2011).
Schuchman et al., "A Novel Use for Acid Ceramidase in Cell-Based Therapies for Degenerative Joint Diseases, Including the Mucopolysaccharidoses," Molecular Genetics and Metabolism 105:S56 (2012) (abstract only).
Grassméet al., "Rhinoviruses Infect Human Epithelial Cells via Ceramide-Enriched Membrane Platforms," J. of Biological Chemistry 280(28)(Issue of Jul. 15):26256-26262 (2005).
Gassert et al., "Induction of Membrane Ceramides: A Novel Strategy to Interfere with T Lymphocyte Cytoskeletal Reorganization in Viral Immunosuppression," PLoS Pathogens 5(10):1-11 (2009).
Gulbins et al., "Ceramide, Membrane Rafts and Infections," J. Mol. Med. 82:357-363 (2004).
Simons et al., "Cholesterol, Lipid Rafts, and Disease," J. of Clinical Investigation 110(5):597-603 (2002).
Becker et al., "Ceramide in Pseudomonas aeruginosa Infections and Cystic Fibrosis," Cell Physiol. Biochem. 26:57-66 (2010).
Esen et al., "Mechanisms of Staphylococcus aureus Induced Apoptosis of Human Endothelial Cells," Apoptosis 6(6):431-439 (2001).
Grassméet al., "Acidic Sphingomyelinase Mediates Entry of N. gonorrhoeae into Nonphagocytic Cells," Cell 91:605-615 (1997).
Grassméet al., "Host Defense Against Pseudomonas aeruginosa Requires Cermaide-Rich Membrane Rafts," Nature Medicine 9(3):322-330 (2003).
Dreschers et al., "Infections with Human Rhinovirus Induce the Formation of Distinct Functional Membrane Domains," Cell Physiol. Biochem. 20:241-254 (2007).
English Translation and Notice of Reasons for Rejection for Japanese Application No. 2014-517125 (dated May 9, 2016).
Office Action for U.S. Appl. No. 14/516,231 (dated Jun. 22, 2016).
Cameron, E.R., "Recent Advances in Transgenic Technology," Molecular Biotechnol. 7:253-265 (1997).
Couzin et al., "As Gelsinger Case Ends, Gene Therapy Suffers Another Blow," Science 307:1028 (2005).
Donsante et al., "AAV Vector Integration Sites in Mouse Hepatocellular Carcinoma," Science 317:477 (2007).
Juengst, E.T., "What Next for Human Gene Therapy?," BMJ 326:1410-11 (2003).
Kappel et al., "Regulating Gene Expression in Transgenic Animals," Current Opinion in Biotechnology 3:548-53 (1992).
Kimmelman, J., "Recent Developments in Gene Transfer: Risk and Ethics," BMJ 350:79-82 (2005).
Mullins et al., "Transgenesis in Nonmurine Species," Hypertension 22(4):630-3 (1993).
Mullins et al., "Transgenesis in the Rat and Larger Mammals," J. Clin. Invest. 97(7):1557-60 (1996).
Raper, S.E., "Gene Therapy: The Good, the Bad, and the Ugly," Surgery 137(5):487-92 (2005).
Rosenberg et al., "Gene Therapist, Heal Thyself," Science 287:1751 (2000).
Touchette, N., "Gene Therapy: Not Ready for Prime Time," Nature Medicine 2(1):7-8 (1996).
Wigley et al., "Site-Specific Transgene Insertion: An Approach," Reprod. Fertil. Dev. 6:585-8 (1994).
Wolff, J.A., "The 'Grand' Problem of Synthetic Delivery," Nat. Biotechnol. 20:768-9 (2002).
Office Action for U.S. Appl. No. 14/776,442 (dated May 17, 2017).
Office Action for European Patent Application No. 14775400.6 (dated Jun. 14, 2017).
Office Action for European Patent Application No. 12830086.0 (dated Oct. 2, 2017).
English Translation and Third Office Action for Chinese Patent Application No. 201380031825.3 (dated Oct. 10, 2017).
Schulze et al., "Overexpression and Mass Spectrometry Analysis of Mature Human Acid Ceramidase," Biol. Chem. 388:1333-43 (2007).
Office Action for U.S. Appl. No. 15/490,053 (dated Mar. 9, 2018).
Office Action for European Patent Application No. 13797635.3 (dated Oct. 4, 2018).
Pewzner-Jung et al., "Sphingoid Long Chain Bases Prevent Lung Infection by Pseudomonas aeruginosa," EMBO Mol. Med. 6(9):1205-14 (2014).

* cited by examiner

A.
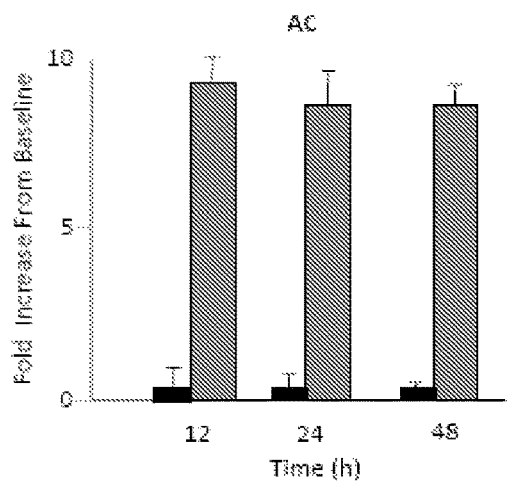
B.
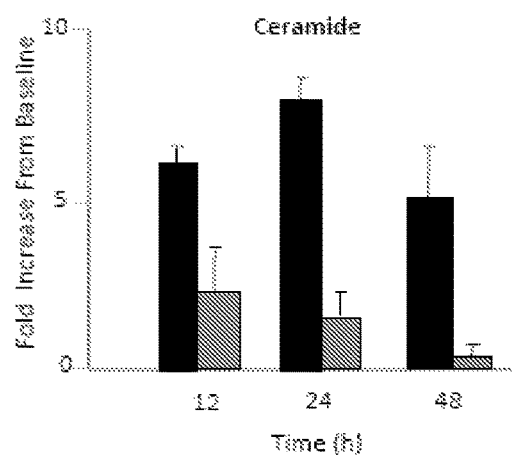
C.
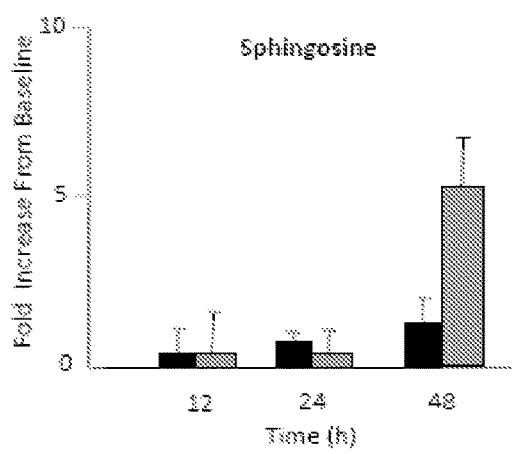
Figures 1A–C

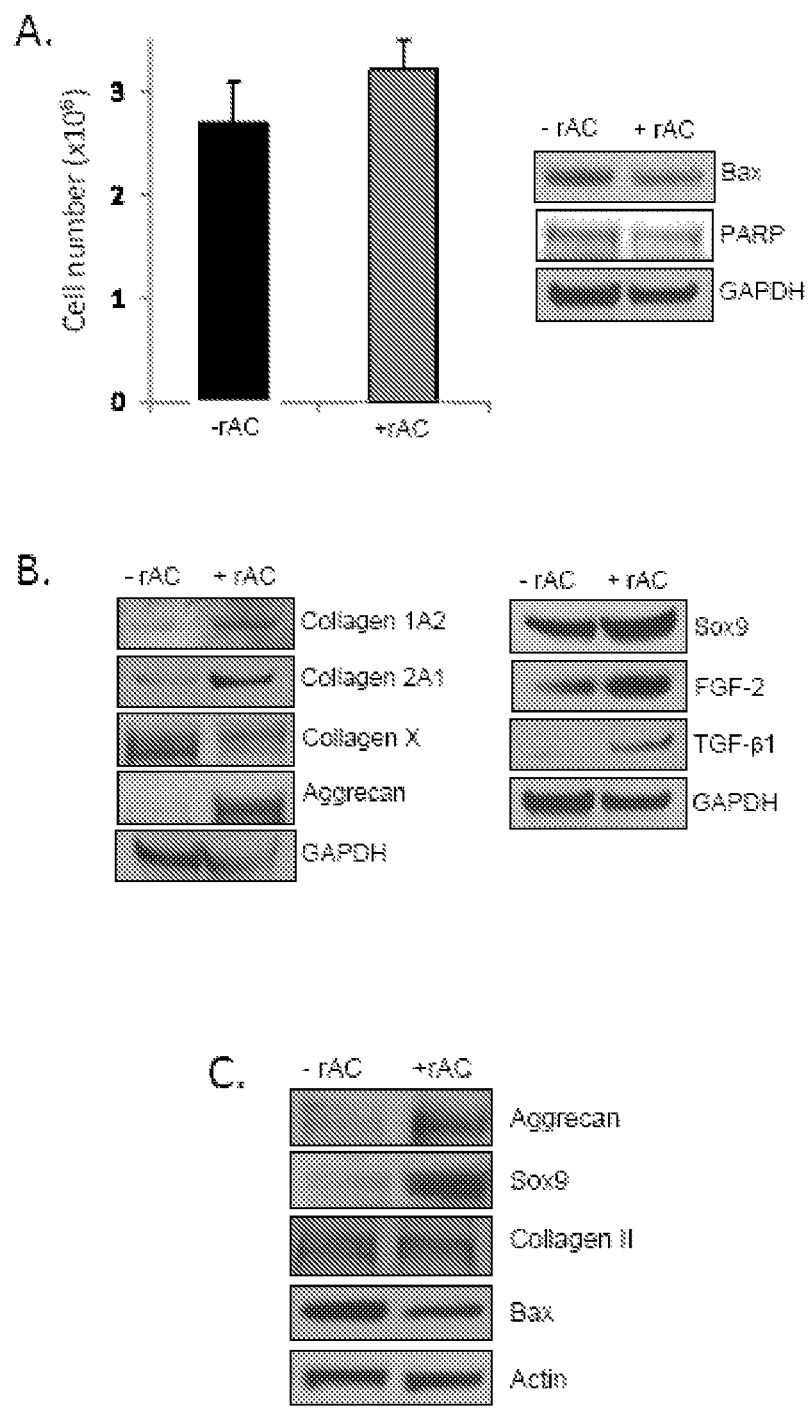
Figures 2A–C

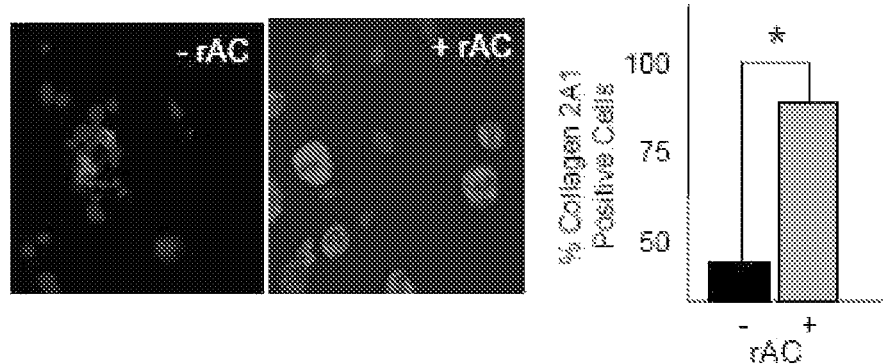
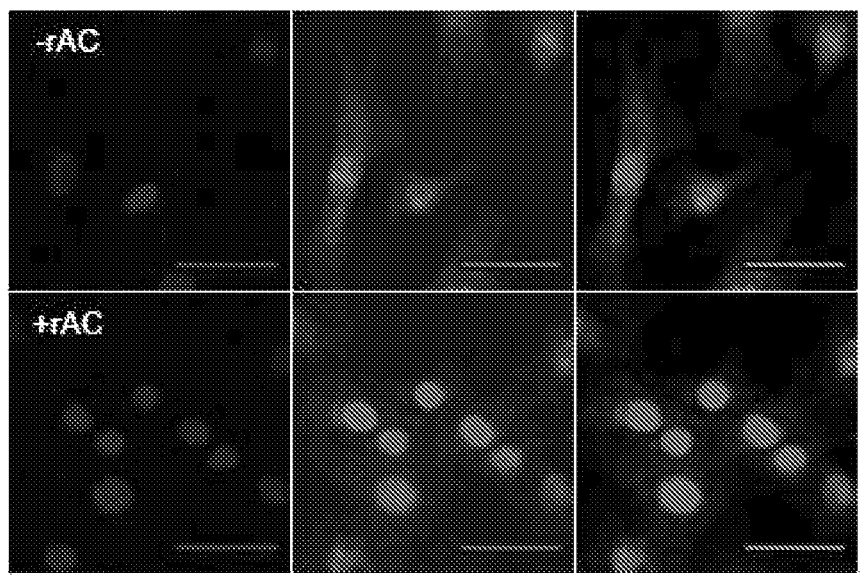
Figures 3A–B

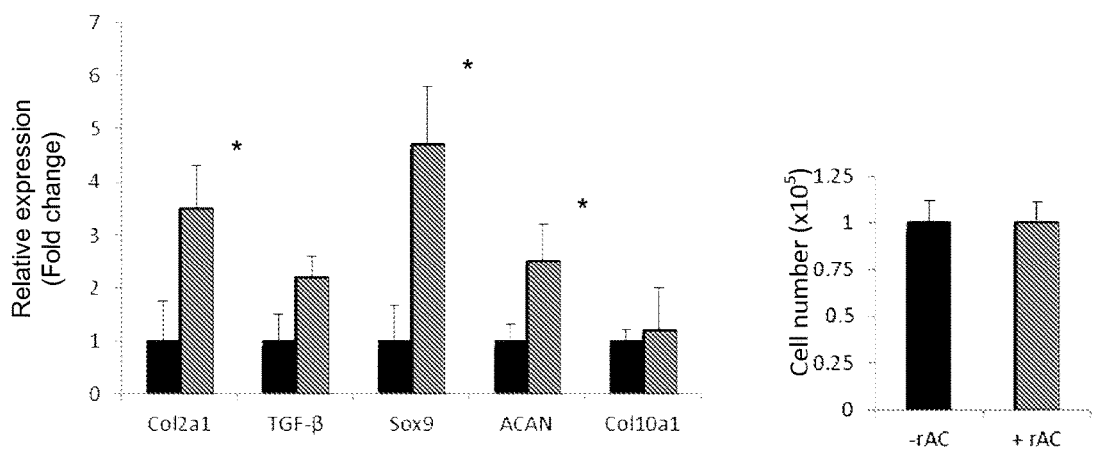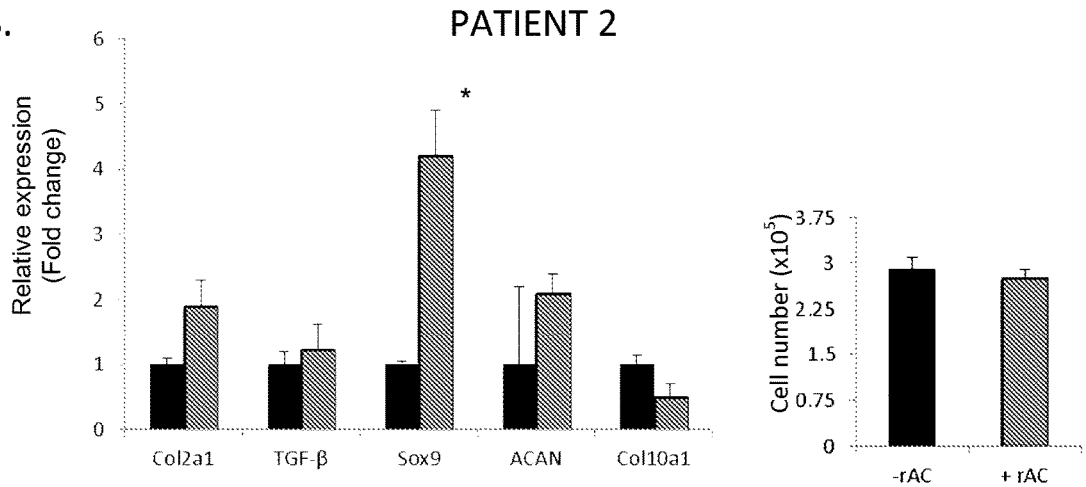
Figures 4A–B

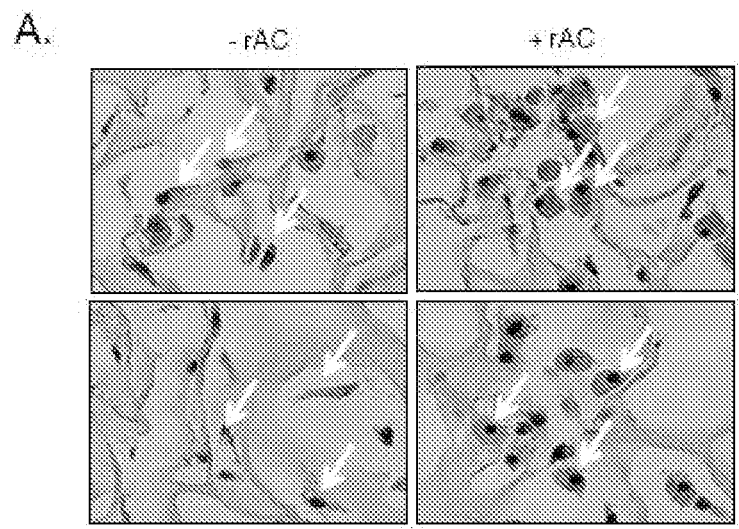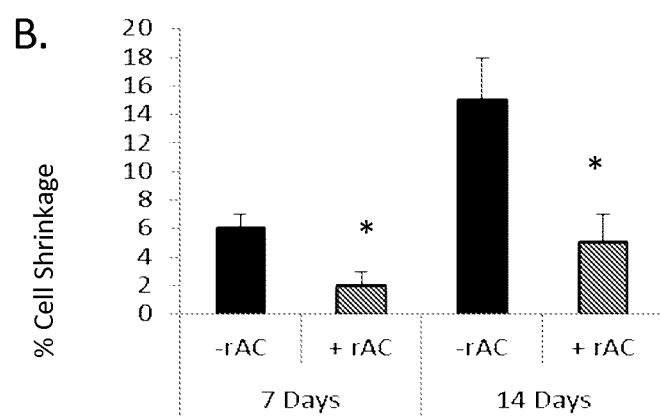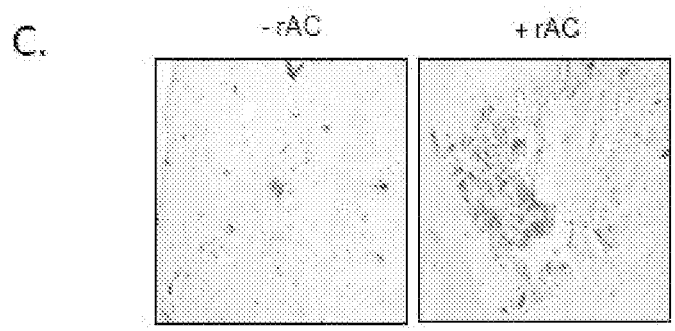
Figures 5A–C

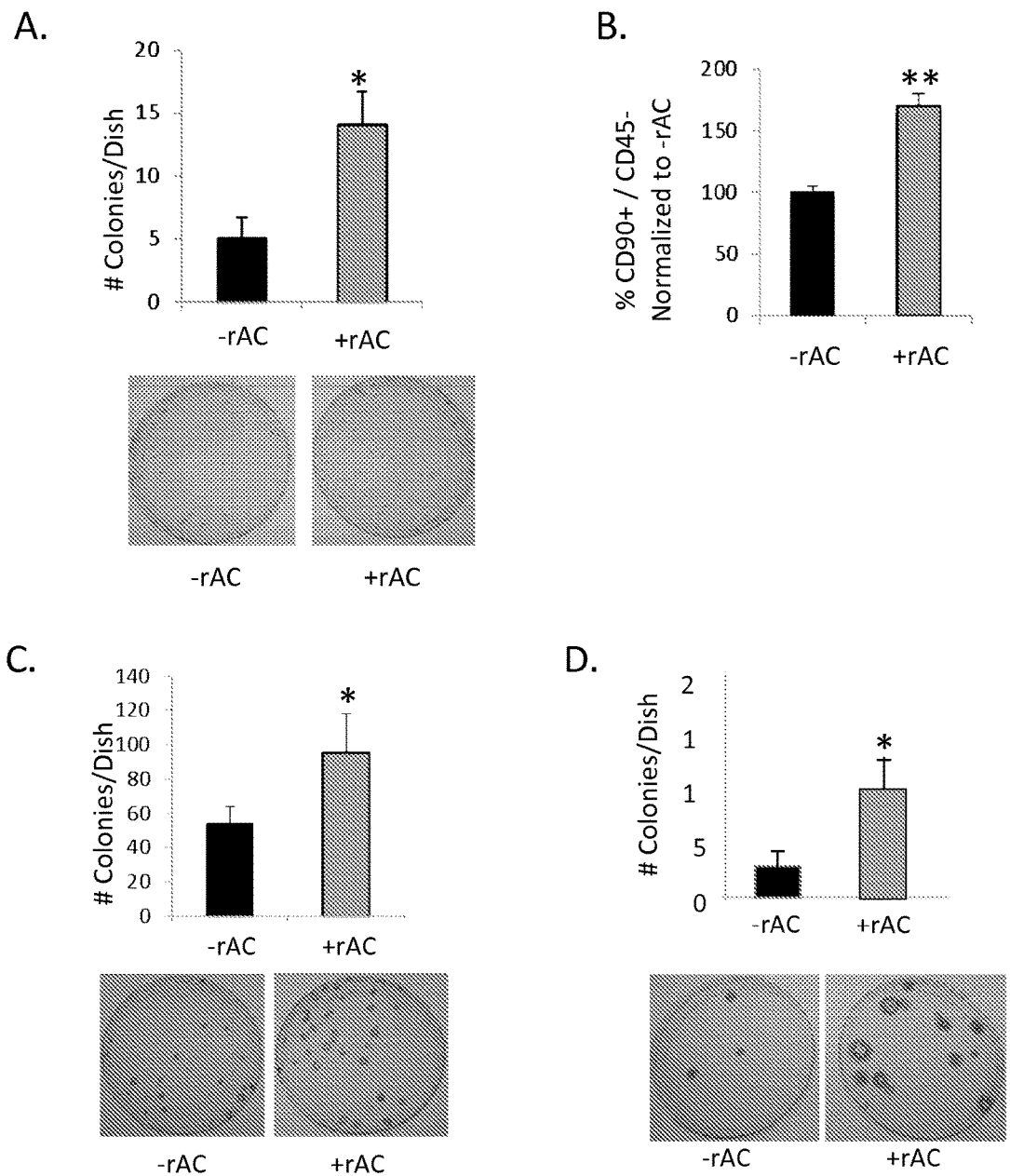
Figures 6A–D

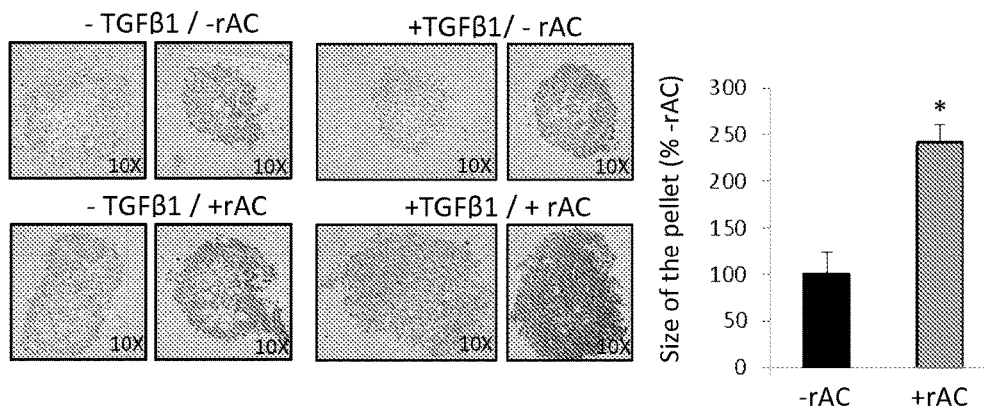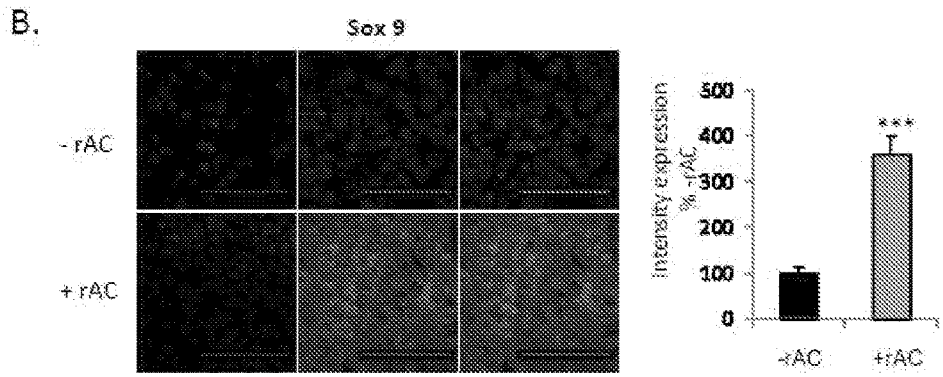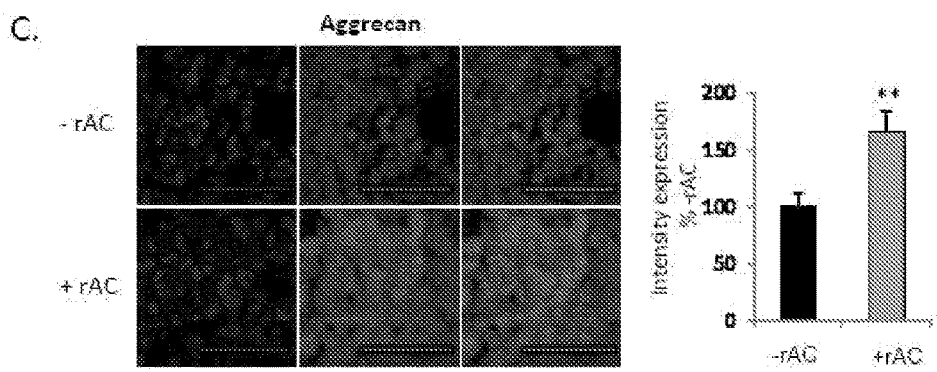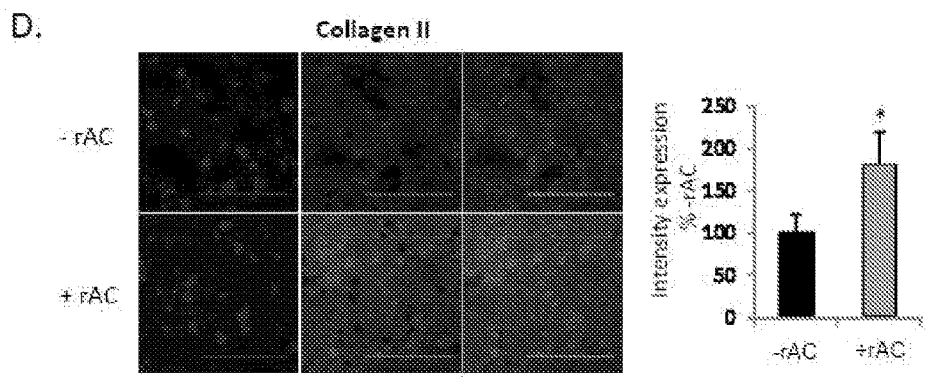
Figures 7A–D

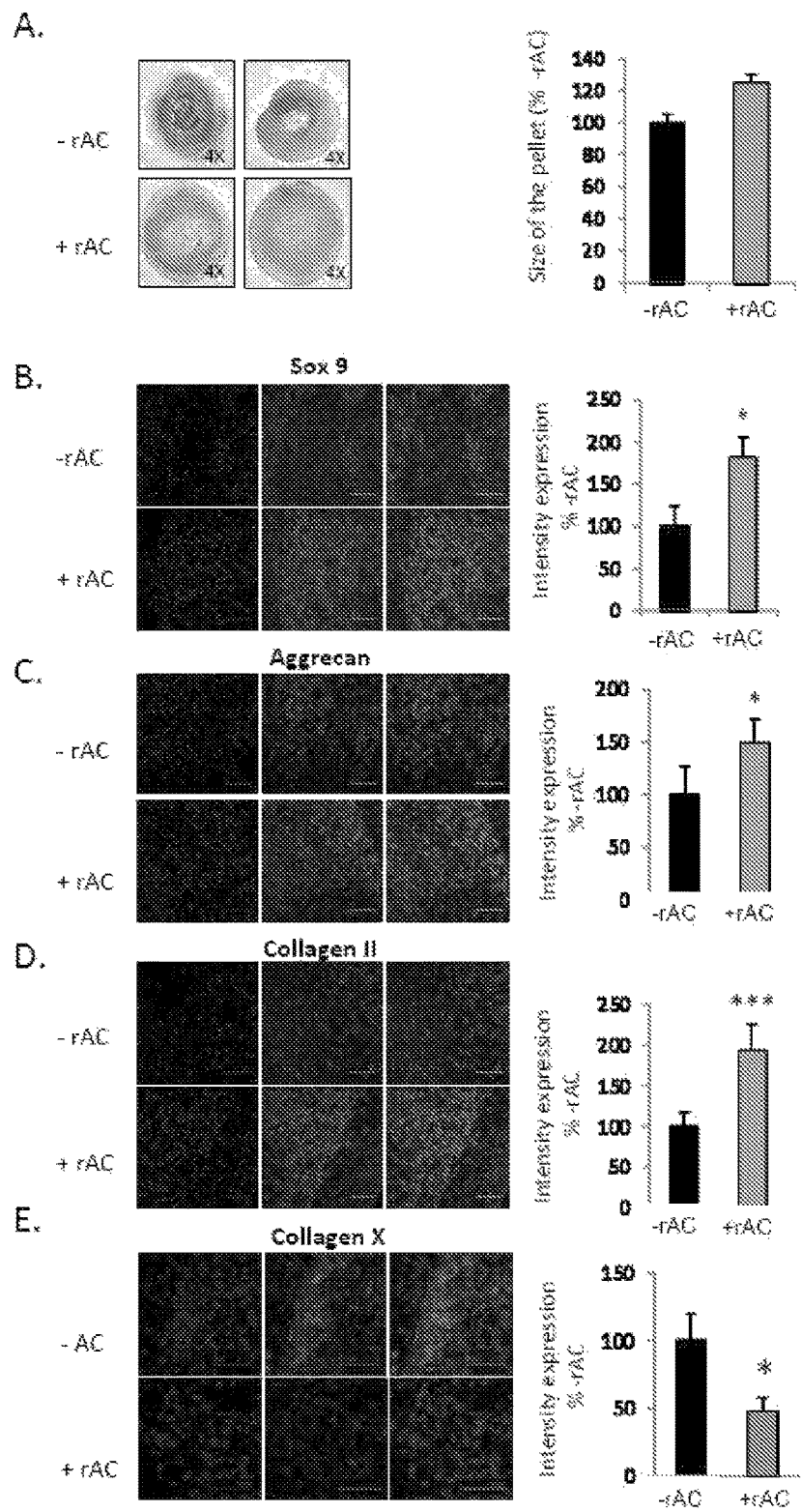
Figures 8A–E

CERAMIDASE AND CELL DIFFERENTIATION

This application is a national stage application under 35 U.S.C. § 371 of PCT Application No. PCT/US2012/054316, filed Sep. 7, 2012, which claims the benefit of U.S. Provisional Patent Application Ser. No. 61/531,917, filed Sep. 7, 2011, all of which are hereby incorporated by reference in their entirety.

FIELD OF THE INVENTION

This invention relates to ceramidase and cell differentiation.

BACKGROUND OF THE INVENTION

Cell-based therapy for cartilage repair has gained increasing popularity since the first reports of successful autologous chondrocyte implantation (ACI) over 10 years ago (Minas et al., "Chondrocyte Implantation in the Repair of Chondral Lesions of the Knee: Economics and Quality of Life," *Am. J. Orthop.* 27(11):739-44 (1998)). In ACI, primary chondrocytes are obtained from small biopsies of healthy articular cartilage, expanded, and then placed onto three-dimensional scaffolds for subsequent use in cartilage repair surgery (see Vavken et al., "Effectiveness of Autologous Chondrocyte Implantation in Cartilage Repair of the Knee: A Systematic Review of Controlled Trials," *Osteoarthritis Cartilage* 18(6):857-63 (2010)). Currently, ACI is used in approximately 10% of all cartilage repair procedures performed world-wide where the lesions are less than 2-4 cm$^2$ (Cole et al., "Outcomes After a Single-Stage Procedure for Cell-based Cartilage Repair: A Prospective Clinical Safety Trial With 2-year Follow-up," *Am. J. Sports Med.* 39(6): 1170-79 (2011)). ACI has also been used in veterinary medicine to improve the outcome of cartilage repair surgery in large (equine) and small (dog) animals (Breinan et al., "Autologous Chondrocyte Implantation in a Canine Model: Change in Composition of Reparative Tissue With Time," *J. Orthop. Res.* 19(3):482-92 (2001); Frisbie et al., "Evaluation of Autologous Chondrocyte Transplantation Via a Collagen Membrane in Equine Articular Defects: Results at 12 and 18 Months," *Osteoarthritis Cartilage* 16(6):667-79 (2008)). There have been many reports documenting the improved clinical effectiveness of ACI as compared to other cartilage repair procedures, and several large, multi-site clinical studies are currently underway (Ebert et al., "Clinical and Magnetic Resonance Imaging-based Outcomes to 5 Years After Matrix-induced Autologous Chondrocyte Implantation to Address Articular Cartilage Defects in the Knee," *Am. J. Sports Med.* 39(4):753-63 (2011)). An important limitation of this procedure, however, is the requirement of two invasive surgeries, the first of which requires extraction of cells from healthy cartilage tissue, and the second to implant the cells that have been expanded ex vivo. Recent research has therefore focused on the use of alternative chondrocyte sources where the cells can be obtained less invasively (e.g., nasoseptal (Bichara et al., "Porouspoly (Vinyl Alcohol)-alginate Gel Hybrid Construct for Neocartilage Formation Using Human Nasoseptal Cells," *J. Surg. Res.* 163(2):331-6 (2010))), the generation of chondrocytes from adult stem cells (e.g., mesenchymal stem cells (MSCs) from the bone marrow or adipose tissue), and/or the use of MSCs directly for transplantation (Augello et al., "Mesenchymal Stem Cells: A Perspective From In Vitro Cultures to In Vivo Migration and Niches," *Eur. Cell Mater.* 20:121-33 (2010); Chanda et al., "Therapeutic Potential of Adult Bone Marrow-derived Mesenchymal Stem Cells in Diseases of the Skeleton," *J. Cell Biochem.* 111(2):249-57 (2010); Hildner et al., "State of the Art and Future Perspectives of Articular Cartilage Regeneration: A Focus on Adipose-derived Stem Cells and Platelet-derived Products," *J. Tissue Eng. Regen. Med.* 5(4):e36-51 (2011)).

A key factor in the development of any cell-based therapy is to find safe and effective methods to rapidly expand autologous cells in a manner that retains their phenotype and in vivo repair potential. For ACI, research has concentrated on defining the culture media and growth factors used for articular chondrocyte expansion, as well as the improved design and formulation of scaffolds used to adhere the cells and prepare them for surgical re-implantation. Currently, most culture medias used to expand primary articular chondrocytes contain serum supplemented with growth factors, including members of the transforming growth factor (TGF) (β1, β2, and β3) and bone morphogenic families (BMP) (2,4,6,12,13), insulin growth factor 1 (IGF1), fibroblast growth factor 2 (FGF2) and others (see Umlauf et al., "Cartilage Biology, Pathology, and Repair," *Cell Mol. Life Sci.* 67(24):4197-211 (2010)). Similarly, numerous transcription factors influence chondrogenesis, including Sox9, β-catenin, Smads, and others, resulting in optimal expression of chondrocyte-specific markers. Sox9 in particular is required for pre-cartilage condensation and differentiation of chondroprogenitor cells into chondroblasts (Lee et al., "Sox9 Function in Craniofacial Development and Disease," *Genesis* 49(4):200-8 (2011)).

Evaluation of chondrocyte quality from these various cell culture procedures generally relies on documenting the expression of chondrocyte-specific markers, including various collagens (e.g., I and II), extracellular matrix components (e.g., aggregan), and growth and transcription factors known to influence chondrogenesis. Unfortunately, although many different culture systems have been used to evaluate chondrogenesis in vitro, no consensus method exists and current procedures are not very effective at maintaining the chondrogenic phenotype during the expansion period.

Similarly, many different methods have been used to expand and differentiate MSCs into chondrocytes. Since MSCs represent a very small fraction of the total bone marrow (BM) cell population, they must be enriched by techniques such as flow cytometry, or expanded in culture to obtain enough cells for transplantation. These procedures increase the risk of transformation and/or contamination of the stem cell population. In addition, following the initial expansion they must undergo an in vitro differentiation period of several additional weeks, and the chondrogenic potential of these "induced" chondrocytes remains in question (Dashtdar et al., "Preliminary Study Comparing the Use of Allogenic Chondrogenic Pre-differentiated and Undifferentiated Mesenchymal Stem Cells for the Repair of Full Thickness Articular Cartilage Defects in Rabbits," *J. Orthop. Res.* 29(9):1336-42 (2011)).

The present invention is directed to overcoming these and other deficiencies in the art.

SUMMARY OF THE INVENTION

A first aspect of the present invention relates to a method of producing chondrocytes. This method involves selecting a population of cells having the potential to differentiate into chondrocytes, and treating the selected cell population with a ceramidase to transform one or more of the cells in the selected population into chondrocytes.

A second aspect of the present invention relates to a method of improving the phenotype of a chondrocyte population. This method includes selecting a population of chondrocytes having a poor chondrocytic phenotype, and treating the selected cell population with a ceramidase to improve the chondrocytic phenotype of the population.

A third aspect of the present invention relates to a method of promoting chondrogenesis. This method includes selecting a population of bone marrow cells in need of differentiation into chondrocytes, first treating the population of bone marrow cells with a ceramidase to enrich mesenchymal stem cells within the bone marrow cell population, and second treating the population of enriched mesenchymal stem cells with a ceramidase, or a ceramidase and TGFβ, to promote differentiation of mesenchymal stem cells into chondrocytes.

A fourth aspect of the present invention relates to a method of maintaining a cell population in a differentiated state or increasing the number of cells of a population in a differentiated state. This method includes selecting a cell population in need of being maintained in a differentiated state or a cell population in need of an increased number of cells in a differentiated state, and treating the selected cell population with a ceramidase to maintain or increase the number of differentiated cells in the selected cell population.

A fifth aspect of the present invention relates to a method of producing a population of differentiated cells. This method includes selecting a population of stem cells capable of differentiating into a desired population of differentiated cells, selecting a differentiation medium capable of stimulating differentiation into the desired differentiated cells, and culturing the population of stem cells in the differentiation medium and ceramidase to stimulate differentiation into the population of differentiated cells.

Research has been focused on enzymes involved in the metabolism of sphingolipids, a group of over 100 lipids that share a common sphingoid base backbone (sphingosine) and have important effects on cell survival and differentiation (e.g., Nikolova-Karakashian et al., "Sphingolipid Metabolism, Oxidant Signaling, and Contractile Function of Skeletal Muscle," *Antioxid. Redox Signal* 15(9):2501-17 (2011), which is hereby incorporated by reference in its entirety). For example, ceramide is a potent pro-apoptotic lipid that disrupts and reorganizes membrane-embedded signaling platforms, while sphingosine-1-phosphate (S1P) is a proliferative lipid that can be secreted from cells and has potent mitogenic activities. An intermediate in the conversion of ceramide to S1P is sphingosine itself, another important signaling lipid. Ceramidases are a class of enzymes that hydrolyze ceramide into sphingosine, which is subsequently converted into S1P (Mao et al., "Ceramidases: Regulators of Cellular Responses Mediated by Ceramide, Sphingosine, and Sphingosine-1-phosphate," *Biochem. Biophys. Acta* 1781(9):424-34 (2008), which is hereby incorporated by reference in its entirety). Importantly, the only way that cells can generate sphingosine is by ceramide hydrolysis via ceramidases (Okino et al., "The Reverse Activity of Human Acid Ceramidase," *J. Biol. Chem.* 278(32):29948-53 (2003), which is hereby incorporated by reference in its entirety). Thus, these enzymes play critical roles in regulating these lipid signaling pathways.

Acid ceramidase (AC, EC#3.5.1.23) is one of five known mammalian ceramidases, each of which has been defined by their unique pH optima and/or intracellular locations. AC has historically been the most extensively studied ceramidase due to its involvement in the human genetic disorder that results from its deficiency, Farber Lipogranulomatosis (FD, MIM #228000). FD is an extremely rare disorder, and surviving patients often present with juvenile arthritis and degenerating joint disease associated with the accumulation of inflammatory nodules. Tracheal abnormalities also have been described, suggesting an important role for AC in hyaline cartilage development.

Several other studies have demonstrated the importance of sphingolipid signaling on cartilage homeostasis. For example, an early report (Sabatini et al., "Effects of Ceramide on Apoptosis, Proteoglycan Degradation, and Matrix Metalloproteinase Expression in Rabbit Articular Cartilage," *Biochem. Biophys. Res. Commun.* 267(1):438-444 (2000), which is hereby incorporated by reference in its entirety) showed that a synthetic ceramide derivative (C2 ceramide) stimulated the expression of MMP-1, 3, and 13 in rabbit articular chondrocytes, and induced chondrocyte apoptosis. Gilbert et al. also showed that treatment of bovine articular chondrocytes with sphingomyelinase, an enzyme that produces ceramide by sphingomyelin hydrolysis, decreased expression of collagen II (Gilbert et al., "Sphingomyelinase Decreases Type II Collagen Expression in Bovine Articular Cartilage Chondrocytes Via the ERK Signaling Pathway," *Arthritis Rheum.* 58(1):209-220 (2008), which is hereby incorporated by reference in its entirety). Elevated ceramide has also been documented in patients with rheumatoid and osteoarthritis (Ciurtin et al., "Correlation Between Different Components of Synovial Fluid and Pathogenesis of Rheumatic Diseases," *Rom. J. Intern. Med.* 44(2):171-81 (2006), which is hereby incorporated by reference in its entirety), and inhibition of S1P production in induced rodent models of arthritis has led to beneficial clinical results (Fitzpatrick et al., "Attenuation of Arthritis in Rodents by a Novel Orally-available Inhibitor of Sphingosine Kinase," *Inflammopharmacology* 19(2):75-87 (2011), which is hereby incorporated by reference in its entirety).

In addition, it has been found that animals with genetic deficiencies of enzymes involved in glycosaminoglycan (GAG) degradation (i.e., the mucopolysaccharidoses, MPS), have numerous abnormalities in sphingolipid metabolism in their connective tissues. For example, chondrocyte apoptosis and cartilage degradation in the MPS animals is associated with elevated ceramide, while synovial hyperplasia is associated with elevated S1P (Simonaro et al., "Mechanism of Glycosaminoglycan-mediated Joint and Bone Disease: Implications for the Mucopolysaccharodoses and Other Connective Tissue Diseases," *Am. J. Path.* 172:112-122 (2008), which is hereby incorporated by reference in its entirety). Elevated AC activity can also be detected in serum and synovial fluid from the MPS animals, likely a response to the elevated ceramide.

To further study the role of AC in cell signaling and disease, a complete AC knockout mouse was constructed several years ago and it was found that embryos lacking AC could not survive beyond the 4-cell stage and underwent apoptosis (Eliyahu et al., "Acid Ceramidase is a Novel Factor Required for Early Embryo Survival," *FASEB J.* 21(7):1403-9 (2007), which is hereby incorporated by reference in its entirety). This led to evaluation of the effects of recombinant AC (rAC) on oocyte and embryo survival in vitro, revealing that supplementation of media with this enzyme could slow apoptosis and increase cell and/or embryo survival (Eliyahu et al., "Acid Ceramidase Improves the Quality of Oocytes and Embryos and the Outcome of In Vitro Fertilization," *FASEB J.* 24(4):1229-38 (2010), which is hereby incorporated by reference in its entirety). Subsequent studies have evaluated the anti-apoptosis effects of rAC on other primary cells, including hippocampal neurons treated with the Aβ protein (He et al., "Deregulation of Sphingolipid Metabolism in Alzheimer's Disease," *Neurobiol. Aging* 31(3):398-408 (2010), which is hereby incorporated by reference in its entirety) and mouse embryonic stem cells.

Ceramidases regulate the metabolism of several important bioactive lipids, including ceramide, sphingosine, and sphingosine-1-phosphate. The present invention shows that addition of recombinant rAC as a media supplement markedly improved the chondrogenic phenotype of expanded rat and horse articular chondrocytes, as well as human chondrocytes obtained from aged patients with osteoarthritis. The chondrocyte phenotype was assessed by a combination of histochemical staining (Alcian Blue and Safranin O), western blotting (e.g., Sox9, aggrecan, collagen IIA1, TGFβ1, FGF2, etc.), and/or qPCR. The effects of rAC were evident in monolayer and three-dimensional cultures, including cells grown on collagen scaffolds and fibrin gels. rAC also reduced the number of apoptotic cells in some culture conditions, contributing to overall improved cell quality. It is demonstrated herein that rat, equine, and human articular chondrocytes treated once with rAC in either monolayer cultures or three-dimensional scaffold systems had an improved chondrogenic phenotype after 2-3 week cell expansion, including enhanced expression of Sox9, FGF2, collagen II, aggregan and other chondrogenic markers.

In addition to these effects on primary chondrocytes, rAC had a significant impact on bone marrow-derived mesenchymal stem cells (MSCs). Here, it is shown that rat, feline, and equine bone marrow cells grown for only one week in the presence of rAC yield about two-fold more MSCs, and that rAC led to enhanced chondrogenesis of MSCs. When rAC was added to freshly harvested bone marrow cultures, an approximate two-fold enrichment of MSCs was observed by one-week. rAC also improved the chondrogenic differentiation of MSCs, as revealed by histochemical and immunostaining. These effects were observed using both rat and horse cells, and were synergistic with TGFβ1. These results demonstrate that rAC is an important supplement that could be used to improve the quality of cells used for cell-based cartilage repair, and can be useful in vivo to induce endogenous cartilage repair in combination with other techniques. Thus, rAC can be included in media used to culture primary chondrocytes and/or MSC chondrocyte differentiation media to improve the production and chondrogenic potential of these cells for cartilage repair. rAC also may added to three-dimensional scaffolds to induce and/or enhance chondrogenesis of cells in vivo. It is expected that other ceramidases may also be used for these purposes.

BRIEF DESCRIPTION OF THE DRAWINGS

FIGS. 1A-1C are graphs illustrating the effect of rAC on AC (FIG. 1A), ceramide (FIG. 1B), and sphingosine (FIG. 1C) activity of primary rat articular chondrocytes. Data were collected at 12 hours, 24 hours, and 48 hours. Samples with rAC ($^+$rAC) are indicated with gray bars and samples without rAC ($^-$rAC) are indicated with black bars. Primary rat articular chondrocytes were isolated and grown in monolayer cultures for 48 hours with or without rAC (rAC, 200 U/ml) added to the media. At the indicated times, proteins and lipids were extracted from the cells, and the AC activity (FIG. 1A), ceramide (FIG. 1B), and sphingosine (FIG. 1C) levels were determined. The addition of rAC to the culture media led to markedly increased AC activity that was sustained for at least 48 hours. In addition, by 12 hours ceramide levels were elevated, but significantly less in cells treated with rAC (i.e., by 48 hours cells treated with rAC had no detectable ceramide elevation). Finally, the levels of sphingosine, the product of ceramide hydrolysis by AC, was elevated in rAC-treated cells by 48 hours.

FIGS. 2A-2C show chondrogenic marker expression in rat articular chondrocytes. FIG. 2A illustrates total cell counts for cultures of rat articular chondrocytes with and without recombinant human AC (rAC) (left panel), and western blot results for Bax, PARP, and GAPDH in cultures of rat articular chondrocytes with and without rAC (right panel). Rat articular chondrocytes were obtained from femurs and grown for three weeks in monolayer cultures using standard culture medium with or without recombinant human AC (rAC 200 U/ml). rAC was added once at the initiation of the cultures. At the end of the three-week expansion period, the cells were harvested and analyzed. Total cell counts revealed no significant differences in the presence of rAC. Western blotting for two apoptosis markers (Bax and PARP) similarly revealed no differences. FIG. 2B shows western blots of expanded chondrocytes for chronogenic markers. The expanded chondrocytes were analyzed by western blot for several important chondrogenic markers, including collagens 1A2 and 2A1, aggrecan, Sox9, FGF-2, and TGFβ1. In all cases, these chondrocyte markers were elevated in the cells treated with rAC. Collagen X is expressed at high levels in fibroblasts, but not in chondrocytes (i.e., a "reverse" marker of chondrogenesis). In contrast to collagens 2A1 and 1A2, collagen X expression was not significantly altered by rAC treatment. FIG. 2C shows western blots of horse articular chondrocytes for chronogenic markers including Aggrecan, Sox9, Collagen II, Bax, and Actin, with and without rAC. Horse articular chondrocytes were obtained surgically from femoral heads and frozen. The frozen cells were then recovered and grown in monolayer cultures for three weeks without rAC. At three weeks, the cells were passaged and re-plated at a density of $1 \times 10^6$, and then grown for an additional one week with or without rAC. At the end of this one-week growth period (P1), the cells were analyzed by western blot, revealing that the expression of two chondrogenic markers, aggrecan and Sox9, were highly elevated in the rAC-treated horse cells. Bax expression also was reduced in the rAC cells, suggesting a reduction in apoptosis by rAC treatment. All experiments were repeated at least three times. Images are representative from individual experiments.

FIGS. 3A-3B relate to the expression of collagen 2A1 in rat chondrocytes, with and without rAC. FIG. 3A shows confocal immunohistochemistry of collagen 2A1 in chondrocytes with and without rAC (left panel), as well as a graphical representation of collagen 2A1 percentage in chondrocytes with and without rAC (right panel), confirming the high level of expression of collagen 2A1 in rat chondrocytes treated with rAC. FIG. 3B shows confocal immunostaining of Sox9 with and without rAC treatment, showing different intracellular distribution of Sox9 two weeks after AC treatment. Blue (DAPI) indicates nuclei, and red indicates collagen 2A1 and Sox9, respectively. Experiments were repeated at least three times. Images are representative from individual experiments. Scale bars: 50 μm. *=p<0.05.

FIGS. 4A-4B relate to chondrogenic markers in primary human chondrocytes in two patients with osteoarthritis. FIG. 4A is a graph comparing various chondrogenic markers (collagen 2A1 (Col2a1), TGFβ, Sox9, aggrecan (ACAN), and collagen X (Col10a1)) in patient 1, with and without rAC treatment (left). Primary human chondrocytes obtained from the femoral head of a 74-year-old woman with osteoarthritis (OA) were expanded for three weeks in monolayer culture with or without rAC added to the culture media (DMEM+10% FBS, rAC added once at the initiation of the culture; 170 U/mlAC). mRNA expression of chondrogenic markers Col2a1, TGFβ1, Sox9, and ACAN were analyzed by RT-PCR. Note the positive influence of rAC on the expression of these markers. The expression of Col10a1 was unchanged in these cultures. The same experiment was repeated on a second set of cells from a patient with osteoarthritis (Patient 2). FIG. 4B depicts a graph comparing those same chondrogenic markers in patient 2, with and without rAC. RT-PCR analysis was performed three times on cells grown in individual wells. Consistent with the results obtained with rat and equine chondrocytes (FIGS. 2A-2C), no significant differences in the number of cells could be found (right panels). *=p<0.05.

FIGS. 5A-5C relate to chondrocytes grown on three-dimensional collagen scaffolds. FIG. 5A shows images of a three-dimensional collagen scaffold on which primary rat chondrocytes were grown. Primary rat chondrocytes were seeded into three-dimensional collagen scaffolds and grown for 7 or 14 days with or without rAC (DMEM containing 10% serum). They were then analyzed for morphology and proteoglycan production by Safranin O staining. The cells grown with rAC were larger and maintained a round phenotype that stained positive with Safranin O (arrows). Shown are representative images from experiments performed three times. FIG. 5B depicts a graphical representation comparing cell shrinkage based on Safranin O and H&E staining at 7 and 14 days, both with and without rAC. The cell shrinkage was evaluated based on Safranin O and H&E staining using the following equation: DNA unit size=π(fiber segment diameter/2)$^2$×(myofiber segment length)/myofiber nuclei. *=p<0.05. FIG. 5C shows primary rat chondrocytes grown in biodegradable fibrin gels with and without rAC. Primary rat chondrocytes were grown for 2 weeks in biodegradable fibrin gels with or without rAC in the culture media. Alcian Blue staining, another marker of proteoglycan expression, indicated enhanced chondrogenesis (more intense blue color). Experiment was performed two times. *=p<0.05.

FIGS. 6A-D relate to mesenchymal stem cells (MSCs) cultured in the presence and absence of rAC. In FIG. 6A, the number of colony forming units in rat bone marrow, both with and without rAC, are shown. Rat bone marrow cells were isolated and grown for one week with or without rAC in standard culture media. rAC was added to the culture media once at the initial plating (5×10E$^6$ cells/cm$^2$). The number of MSCs in the cultures at one week was determined by two assays: the number of fibroblast-like colony forming units (CFU-F) and by flow cytometry. In FIG. 6B, flow cytometry (CD90+/CD45−) in MSCs of rat bone marrow, with rAC and without rAC are shown. An approximate two-three fold increase in the number of rat MSCs was observed using rAC. FIG. 6C shows the number of colony forming units in feline cells (plated at a density of 1-5×10E6 cells/cm$^2$), with rAC and without rAC, while FIG. 6D shows the number of colony forming units in equine cells (plated at 3×10E8 cells/cm$^2$), with and without rAC. *=p<0.05, **=p<0.005.

FIGS. 7A-D relate to isolated rat bone marrow cells used to prepare homogeneous populations of MSCs that were placed into chondrocyte differentiation media, with or without rAC. In FIG. 7A, results of rat bone marrow cells in culture media, either with or without rAC, and with or without TGFβ1, are shown (left panel). FIG. 7A also illustrates a graphical comparison of the pellet area in the presence or absence of rAC with or without TGFβ1 (right panel). Rat bone marrow cells were isolated and expanded for three weeks in standard culture media (without rAC) to prepare homogenous populations of MSCs. They were then placed into chondrocyte differentiation media (Stem Cell Technology) with or without TGFβ1 and/or rAC. Pellet cultures were grown for three weeks to prepare chondrocytes, and then fixed and analyzed by Alcian Blue and Safranin O staining, markers of chondrogenesis. Small and poorly formed pellets in the absence of TGFβ1 and rAC are evident (upper left). TGFβ1 is a standard supplement used to induce the differentiation of bone marrow MSCs to chondrocytes. Addition of TGFβ1 or rAC to the cultures independently had only a modest effect on the pellet size and staining (upper right and lower left). However, inclusion of both proteins in the culture media had a much more significant effect (lower right), both on the size of the pellets and staining intensity. Pellet size is an indicator of the number of chondrocytes, and staining intensity is a measure of proteoglycan deposition. FIGS. 7B-D show immunostaining of rat bone marrow cells against Sox9, aggrecan, and collagen 2A1, respectively. Experiments were performed with three independent rats. Representative images are shown from one experiment. Blue (DAPI) indicates nuclei, and red indicates Sox9, Aggrecan, or Collagen IIA1, respectively. Merged images are to the right. Scale bars: 50 μm. *=p<0.05, =p<0.005, *=p<0.001.

FIGS. 8A-E show results of isolated horse bone marrow cells used to prepare homogeneous populations of MSCs that were placed into chondrocyte differentiation media, with or without rAC. In FIG. 8A, horse bone marrow cells were isolated and expanded for three weeks in standard culture media (without rAC) to prepare homogenous populations of MSCs. They were then placed into chondrocyte differentiation media containing TGFβ1, but with or without rAC. Pellet cultures were grown for three weeks to prepare chondrocytes, and then fixed and analyzed by Alcian Blue and Safranin O staining Smaller, more diffuse pellets in the absence of rAC are evident. Pellets were also submitted to immunostaining against Sox9 (FIG. 8B), Aggrecan (FIG. 8C), or Collagen IIA1 (FIG. 8D). The higher expression intensity of Sox9, Aggrecan, and Collagen IIA1 in the pellets is notable. In FIG. 8E, pellets were also subjected to an immunostaining against Collagen X. Diminished expression of Collagen X in pellets exposed to rAC can be seen. Blue (DAPI) indicates nuclei, and red indicates Sox9, Aggrecan, Collagen IIA1, or Collagen X, respectively. Merged images are to the right. Scale bars: 50 μm. *=p<0.05, =p<0.005, *=p<0.001.

DETAILED DESCRIPTION OF THE INVENTION

A first aspect of the present invention relates to a method of producing chondrocytes. This method involves selecting a population of cells having the potential to differentiate into chondrocytes and treating the selected cell population with a ceramidase to transform one or more of the cells in the selected population into chondrocytes.

Cells having the potential to differentiate into chondrocytes include bone marrow cells, fibroblasts, and mesenchymal stem cells (see Mizushima et al., "Ceramide, a Mediator of Interleukin 1, Tumour Necrosis Factor α, as Well as Fas Receptor Signalling, Induces Apoptosis of Rheumatoid Arthritis Synovial Cells," *Ann. Rheum. Dis.* 57:495-9 (1998), which is hereby incorporated by reference in its entirety).

Suitable cells according to this and all other aspects of the present invention include mammalian cells, e.g., human cells, equine cells, porcine cells, feline cells, and/or canine cells. Human cells are particularly preferred.

In this and all aspects of the present invention involving cell populations, embodiments in which the cells are all of one type, as well as embodiments in which the population is a mixture of two or more cell types, are both contemplated.

Ceramidases hydrolyze the amide linkage of ceramides to generate free fatty acids and sphingoid bases (Nikolova-Karakashian et al., *Methods Enzymol.* 311:194-201 (2000), Hassler et al., *Adv. Lipid Res.* 26:49-57 (1993), which are hereby incorporated by reference in their entirety). There are three types of ceramidases described to date (Nikolova-Karakashian et al., *Methods Enzymol.* 311:194-201 (2000), which is hereby incorporated by reference in its entirety). These are classified as acid, neutral, and alkaline ceramidases according to their pH optimum of enzymatic activity.

Acid ceramidases have optimal enzymatic activity at a pH of 1-5. The murine acid ceramidase was the first ceramidase to be cloned (Koch et al., *J. Biol. Chem.* 271:33110-33115 (1996), which is hereby incorporated by reference in its entirety). It is localized in the lysosome and is mainly responsible for the catabolism of ceramide. Dysfunction of this enzyme because of a genetic defect leads to a sphingolipidosis disease called Farber disease (Koch et al., *J. Biol. Chem.* 271:33110-33115 (1996), which is hereby incorporated by reference in its entirety).

The neutral ceramidases have been purified from rat brain (El Bawab et al., *J. Biol. Chem* 274:27948-27955 (1999), which is hereby incorporated by reference in its entirety) and mouse liver (Tani et al., *J. Biol. Chem* 275:3462-3468 (2000), which is hereby incorporated by reference in its entirety), and were cloned from *Pseudomonas* (Okino et al., *J. Biol. Chem.* 274:36616-36622 (1999), which is hereby incorporated by reference in its entirety), mycobacterium (Okino et al., *J. Biol. Chem.* 274:36616-36622 (1999), which is hereby incorporated by reference in its entirety), mouse (Tani et al., *J. Biol. Chem* 275:11229-11234 (2000), which is hereby incorporated by reference in its entirety), and human (El Bawab et al., *J. Biol. Chem.* 275:21508-21513 (2000), which is hereby incorporated by reference in its entirety). These ceramidases share significant homology, and this homology extends to putative proteins deduced from expressed sequence tag (EST) sequences of *Diciyostelium discoideum* and *Arabidopsis thaliana* (Okino et al., *J. Biol. Chem.* 274:36616-36622 (1999), El Bawab et al., *J. Biol. Chem.* 275:21508-21513 (2000), which are hereby incorporated by reference in their entirety). These ceramidases have a broad pH optimum ranging from 5 to 9 for their activity (Tani et al., *J. Biol. Chem* 275:11229-11234 (2000), El Bawab et al., *J. Biol. Chem.* 275:21508-21513 (2000), which are hereby incorporated by reference in their entirety). They appear to hydrolyze unsaturated ceramide preferentially, saturated ceramide (dihydroceramide) slightly, and hardly hydrolyze phytoceramide (Tani et al., *J. Biol. Chem* 275:11229-11234 (2000), which is hereby incorporated by reference in its entirety). The *Pseudomonas*, mouse, and human neutral ceramidases have a reverse ceramidase activity of catalyzing the formation of ceramide from sphingosine and a fatty acid (Okino et al., *J. Biol. Chem.* 274:36616-36622 (1999), Tani et al., *J. Biol. Chem* 275:11229-11234 (2000), Kita et al., *Biochim. Biophys. Acta* 1485:111-120 (2000), which are hereby incorporated by reference in their entirety). El Bawab et al. (El Bawab et al., *J. Biol. Chem.* 275:21508-21513 (2000), which is hereby incorporated by reference in its entirety) have shown previously that the human neutral ceramidase is localized in the mitochondria.

Alkaline ceramidases have optimal activity at a pH of 9-14. Two alkaline ceramidases were purified from Guinea pig skin epidermis. These two enzymes were membrane bound, and their estimated molecular masses on SDS-PAGE were 60 and 148 kDa, respectively (Yada et al., "Purification and Biochemical Characterization of Membrane-Bound Epidermal Ceramidases from Guinea Pig Skin," *J. Biol. Chem.* 270:12677-12684 (1995), which is hereby incorporated by reference in its entirety). No other studies followed on these two proteins. Two yeast (S. cerevisiae) alkaline ceramidases, phytoceramidase (YPC1p) and dihydroceramidase (YDC1p), were also cloned and partially characterized (Mao et al., "Cloning of an Alkaline Ceramidase from Saccharomyces Cerevisiae. An Enzyme with Reverse (CoA-independent) Ceramide Synthase Activity," *J. Biol. Chem.* 275: 6876-6884 (2000); Mao et al., "Cloning and Characterization of a Saccharomyces Cerevisiae Alkaline Ceramidase with Specificity for Dihydroceramide," *J. Biol. Chem.* 275:31369-31378 (2000), which are hereby incorporated by reference in their entirety). YPC1p was cloned as a high copy suppressor of the growth inhibition of FB1 as it has fumonisin resistant ceramide synthase activity. The second alkaline ceramidase, YDC1p was identified by sequence homology to YPC1p. A database search reveals that YPC1p and YDC1p are not homologous to any proteins with known functions, but are homologous to putative proteins from *Arabidoposis, C. elegans*, peptides deduced from EST sequences of human, mouse, pig, zebra fish, and human genomic sequences. A human homologue has been identified and its cDNA has been cloned. Preliminary results show that this human homologue is also an alkaline ceramidase that selectively hydrolyzes phytoCer.

Ceramidases suitable for use in this and all aspects of the present invention include acid ceramidase (AC), neutral ceramidase, alkali ceramidase, and other ceramidases. In all aspects of the present invention, the ceramidase can be homologous (i.e., derived from the same species) or heterologous (i.e., derived from a different species) to the tissue, cells, and/or subject being treated. Ceramidase (e.g., AC) precursor proteins undergo autoproteolytic cleavage into the active form (composed of α- and β-subunits). This is promoted by the intracellular environment, and, based on highly conserved sequences at the cleavage site of ceramidase precursor proteins across species, is expected to occur in most, if not all, cell types. Thus, ceramidase as used herein includes both active ceramidases and ceramidase precursor proteins, which are then converted into active ceramidase protein. Embodiments in which the precursor protein is taken up by the cell of interest and converted into active ceramidase thereby, as well as embodiments in which the precursor protein is converted into active ceramidase by a different cell or agent (present, for example, in a culture medium), are both contemplated.

Preferably, the ceramidase is an AC (N-acylsphingosine deacylase, I.U.B.M.B. Enzyme No. EC 3.5.1.23). AC protein has been purified from several sources, and the human and mouse cDNAs and genes have been obtained. See Bernardo et al., "Purification, Characterization, and Biosynthesis of Human Acid Ceramidase," *J. Biol. Chem.* 270: 11098-102 (1995); Koch et al., "Molecular Cloning and Characterization of a Full-length Complementary DNA Encoding Human Acid Ceramidase. Identification of the First Molecular Lesion Causing Farber Disease," *J. Biol.*

Chem. 2711:33110-5 (1996); Li et al., "Cloning and Characterization of the Full-length cDNA and Genomic Sequences Encoding Murine Acid Ceramidase," Genomics 50:267-74 (1998); Li et al., "The Human Acid Ceramidase Gene (ASAH): Chromosomal Location, Mutation Analysis, and Expression," Genomics 62:223-31 (1999), all of which are hereby incorporated by reference in their entirety. It is produced through cleavage of the AC precursor protein (see Ferlinz et al., "Human Acid Ceramidase: Processing, Glycosylation, and Lysosomal Targeting," J. Biol. Chem. 276 (38):35352-60 (2001), which is hereby incorporated by reference in its entirety), which is the product of the Asah1 gene (NCBI UniGene GeneID No. 427, which is hereby incorporated by reference in its entirety). ACs and AC precursor proteins that can be used in this and all aspects of the present invention include, without limitation, those set forth in Table 1 below.

ing to U.S. Pat. No. 5,817,789 to Heartlein et al., which is hereby incorporated by reference in its entirety. The chimeric protein can include a ligand domain and the polypeptide agent (e.g., acid ceramidase, other ceramidase, acid ceramidase precursor protein, other ceramidase precursor proteins). The ligand domain is specific for receptors located on a target cell. Thus, when the chimeric protein is delivered to the cell, the chimeric protein will adsorb to the targeted cell, and the targeted cell will internalize the chimeric protein.

In some embodiments, the ceramidase (e.g., AC) may be administered by introducing into the cell a nucleic acid molecule that encodes the ceramidase (either active ceramidase or ceramidase precursor protein, as described above) (JOSEPH SAMBROOK & DAVID W. RUSSELL, 1-3 MOLECULAR CLONING: A LABORATORY MANUAL (3d ed. 2001); SHORT PROTOCOLS IN MOLECULAR BIOLOGY (Frederick M. Ausubel et al. eds., 1999); U.S. Pat. No. 4,237,224 to Cohen & Boyer; each of which

TABLE 1

Exemplary Acid Ceramidase Family Members

| Homo sapiens | | Caenorhabditis elegans | |
|---|---|---|---|
| UniProt | Q13510, Q9H715, Q96AS2 | UniProt | O45686 |
| OMIM | 228000 | IntAct | O45686 |
| NCBI Gene | 427 | NCBI Gene | 173120 |
| NCBI RefSeq | NP_808592, NP_004306 | NCBI RefSeq | NP_493173 |
| NCBI RefSeq | NM_177924, NM_004315 | NCBI RefSeq | NM_060772 |
| NCBI UniGene | 427 | NCBI UniGene | 173120 |
| NCBI Accession | Q13510, AAC73009 | NCBI Accession | O45686, CAB05556 |
| Mus musculus | | Danio rerio | |
| UniProt | Q9WV54, Q3U8A7, Q78P93 | UniProt | Q5XJR7 |
| NCBI Gene | 11886 | NCBI Gene | 450068 |
| NCBI RefSeq | NP_062708 | NCBI RefSeq | NP_001006088 |
| NCBI RefSeq | NM_019734 | NCBI RefSeq | NM_001006088 |
| NCBI UniGene | 11886 | NCBI UniGene | 450068 |
| NCBI Accession | AK151208, AK034204 | NCBI Accession | AAH83231, CB360968 |
| Gallus gallus | | Rattus norvegicus | |
| UniProt | Q5ZK58 | UniProt | Q6P7S1, Q9EQJ6 |
| NCBI Gene | 422727 | NCBI Gene | 84431 |
| NCBI RefSeq | NP_001006453 | NCBI RefSeq | NP_445859 |
| NCBI RefSeq | NM_001006453 | NCBI RefSeq | NM_053407 |
| NCBI UniGene | 422727 | NCBI UniGene | 84431 |
| NCBI Accession | CAG31885, AJ720226 | NCBI Accession | AAH61540, AF214647 |
| Pan troglodytes | | | |
| NCBI Gene | 464022 | | |
| NCBI RefSeq | XP_519629 | | |
| NCBI RefSeq | XM_519629 | | |
| NCBI UniGene | 464022 | | |

Treating according to this aspect of the present invention is carried out by contacting the population of cells with the ceramidase (e.g., AC), using methods that will be apparent to the skilled artisan.

In some embodiments, treating is carried out by introducing into the cells of the population a ceramidase protein. An approach for delivery of proteins or polypeptide agents (e.g., active ceramidase, ceramidase precursor proteins) involves the conjugation of the desired protein or polypeptide to a polymer that is stabilized to avoid enzymatic degradation of the conjugated protein or polypeptide. Conjugated proteins or polypeptides of this type are described in U.S. Pat. No. 5,681,811 to Ekwuribe, which is hereby incorporated by reference in its entirety.

Yet another approach for delivery of proteins or polypeptide agents involves preparation of chimeric proteins accordis hereby incorporated by reference in its entirety). Suitable nucleic acid molecules include, but are not limited to, those set forth in Table 1, supra.

Nucleic acid agents for use in the methods of the present invention can be delivered to a cell in a number of ways known in the art. For example, the nucleic acid can be contained within a vector, e.g., a vector that can be transferred to the cell(s) and provide for expression of the nucleic acid therein. Such vectors include chromosomal vectors (e.g., artificial chromosomes), non-chromosomal vectors, and synthetic nucleic acids. Vectors include plasmids, viruses, and phages, such as retroviral vectors, lentiviral vectors, adenoviral vectors, and adeno-associated vectors.

Nucleic acid agents can be transferred into the cell(s) using ex vivo methods, as will be apparent to the skilled artisan. For example, nucleic acids and vectors can be delivered to cells by physical means, e.g., by electroporation, lipids, cationic lipids, liposomes, DNA gun, calcium phosphate precipitation, injection, or delivery of naked nucleic acid.

As an alternative to non-infective delivery of nucleic acids as described above, naked DNA or infective transformation vectors can be used for delivery, whereby the naked DNA or infective transformation vector contains a recombinant gene that encodes the acid ceramidase/acid ceramidase precursor protein. The nucleic acid molecule is then expressed in the transformed cell.

The recombinant gene includes, operatively coupled to one another, an upstream promoter operable in the cell in which the gene is to be expressed and optionally other suitable regulatory elements (i.e., enhancer or inducer elements), a coding sequence that encodes the nucleic acid, and a downstream transcription termination region. Any suitable constitutive promoter or inducible promoter can be used to regulate transcription of the recombinant gene, and one of skill in the art can readily select and utilize such promoters, whether now known or hereafter developed. The promoter can also be specific for expression in the cell(s) whose survival is to be promoted. Tissue specific promoters can also be made inducible/repressible using, e.g., a TetO response element. Other inducible elements can also be used. Known recombinant techniques can be utilized to prepare the recombinant gene, transfer it into the expression vector (if used), and administer the vector or naked DNA to the cell. Exemplary procedures are described in SAMBROOK & RUSSELL, 1-3 MOLECULAR CLONING: A LABORATORY MANUAL (3d ed. 2001), which is hereby incorporated by reference in its entirety. One of skill in the art can readily modify these procedures, as desired, using known variations of the procedures described therein.

Any suitable viral or infective transformation vector can be used. Exemplary viral vectors include, without limitation, adenovirus, adeno-associated virus, and retroviral vectors (including lentiviral vectors).

Adenovirus gene delivery vehicles can be readily prepared and utilized given the disclosure provided in Berkner, "Development of Adenovirus Vectors for the Expression of Heterologous Genes," *Biotechniques* 6:616-29 (1988); Rosenfeld et al., "Adenovirus-mediated Transfer of a Recombinant a 1-antitrypsin Gene to the Lung Epithelium in Vivo," *Science* 252:431-434 (1991); PCT Publication No. WO/1993/007283 to Curiel et al.; PCT Publication No. WO/1993/006223 to Perricaudet et al.; and PCT Publication No. WO/1993/007282 to Curiel et al., each of which is hereby incorporated by reference in its entirety. Additional types of adenovirus vectors are described in U.S. Pat. No. 6,057,155 to Wickham et al.; U.S. Pat. No. 6,033,908 to Bout & Hoeben; U.S. Pat. No. 6,001,557 to Wilson et al.; U.S. Pat. No. 5,994,132 to Chamberlain & Kumar-Singh; U.S. Pat. No. 5,981,225 to Kochanek & Schniedner; U.S. Pat. No. 5,885,808 to Spooner & Epenetos; and U.S. Pat. No. 5,871,727 to Curiel, each of which is hereby incorporated by reference in its entirety.

Adeno-associated viral gene delivery vehicles can be constructed and used to deliver into cells a recombinant gene encoding a desired nucleic acid. The use of adeno-associated viral gene delivery vehicles in vitro is described in Chatterjee et al., "Dual-target Inhibition of HIV-1 in Vitro by Means of an Adeno-associated Virus Antisense Vector," *Science* 258:1485-8 (1992); Walsh et al., "Regulated High Level Expression of a Human γ-Globin Gene Introduced into Erythroid Cells by an Adeno-associated Virus Vector," *Proc. Nat'l Acad. Sci. USA* 89:7257-61 (1992); Walsh et al., "Phenotypic Correction of Fanconi Anemia in Human Hematopoietic Cells with a Recombinant Adeno-associated Virus Vector," *J. Clin. Invest.* 94:1440-8 (1994); Flotte et al., "Expression of the Cystic Fibrosis Transmembrane Conductance Regulator from a Novel Adeno-associated Virus Promoter," *J. Biol. Chem.* 268:3781-90 (1993); Ponnazhagan et al., "Suppression of Human α-Globin Gene Expression Mediated by the Recombinant Adeno-associated Virus 2-based Antisense Vectors," *J. Exp. Med.* 179:733-8 (1994); Miller et al., "Recombinant Adeno-associated Virus (rAAV)-mediated Expression of a Human γ-Globin Gene in Human Progenitor-derived Erythroid Cells," *Proc. Nat'l Acad. Sci. USA* 91:10183-7 (1994); Einerhand et al., "Regulated High-level Human β-Globin Gene Expression in Erythroid Cells Following Recombinant Adeno-associated Virus-mediated Gene Transfer," *Gene Ther.* 2:336-43 (1995); Luo et al., "Adeno-associated Virus 2-mediated Gene Transfer and Functional Expression of the Human Granulocyte-macrophage Colony-stimulating Factor," *Exp. Hematol.* 23:1261-7 (1995); and Zhou et al., "Adeno-associated Virus 2-mediated Transduction and Erythroid Cell-specific Expression of a Human β-Globin Gene," *Gene Ther.* 3:223-9 (1996), each of which is hereby incorporated by reference in its entirety.

Retroviral vectors which have been modified to form infective transformation systems can also be used to deliver a recombinant gene encoding a desired nucleic acid product into a target cell. One such type of retroviral vector is disclosed in U.S. Pat. No. 5,849,586 to Kriegler & Perez, which is hereby incorporated by reference in its entirety. Lentivirus vectors can also be utilized, including those described in U.S. Pat. No. 6,790,657 to Arya, and U.S. Patent Application Publication No. 2004/0170962 to Kafri et al. and U.S. Patent Application Publication No. 2004/0147026 to Arya, each of which is hereby incorporated by reference in its entirety.

The amount of ceramidase to be used will, of course, vary depending upon the particular conditions. Generally, the ceramidase is used in an amount sufficient to produce chondrocytes. The amount required to obtain the desired effect may vary depending on the cell type, culture conditions, and duration for which it is desired that chondrocytes be produced. Effective amounts can be determined empirically by those of skill in the art. For example, this may involve assays in which varying amounts of ceramidase are administered to cells in culture and the concentration effective for obtaining the desired result is calculated.

Ceramidase (e.g., AC) treatment can be carried out as frequently as required and for a duration that is suitable to promote differentiation into chondrocytes. For example, treatment can be carried out once, or multiple times.

In at least one embodiment, the method further includes treating the selected cell population with one or more transforming growth factors beta (TGFβ) together with ceramidase. TGFβ proteins regulate various aspects of embryonic development and are expressed in the environment of sympathoadrenal progenitor cells (Wall et al., "TGF-beta Related Genes in Development," *Curr. Opin. Genet. Dev.* 4:517 (1994), which is hereby incorporated by reference in its entirety). TGFβ proteins are recognizable by C-terminus polypeptide homology and their signaling via the Similar to Mothers Against Decapentaplegic (SMAD) proteins after binding TGFβ receptors. Examples include TGFβ1-3, bone morphogenenic proteins (BMPs), etc. In some systems, TGFβ regulates expression of parathyroid hormone-related protein (PTHrP) (Pateder et al., "PTHrP Expression in Chick Sternal Chondrocytes is Regulated by TGF-beta Through Smad-mediated Signaling," *J. Cell*

*Physiol.* 188:343 (2001), which is hereby incorporated by reference in its entirety). Bone morphogenic proteins (BMP) and growth and differentiation factors (GDFs) are believed to play a central role during skeletogenesis, including joint formation (Francis-West et al., "BMP/GDF-signalling Interactions During Synovial Joint Development," Cell Tissue Res. 296(1):111-119 (1999); see U.S. Patent Pub. No. 2011/0129867 to Thies, both of which are hereby incorporated by reference in their entirety).

In at least one embodiment, treating involves culturing the cell population in a culture medium containing the ceramidase, a nucleic acid molecule encoding the ceramidase, and/or a cell that contains (and expresses) the nucleic acid molecule and which secretes the ceramidase into the culture medium.

Treating according to this and all aspects of the present invention may be carried out in vitro or in vivo. In vivo treatments include, for example, embodiments in which the population of cells is present in a mammalian subject. In such embodiments the population of cells can be either autologous (produced by the subject), homologous, or heterologous. Suitable subjects according to these embodiments include mammals, e.g., human subjects, equine subjects, porcine subjects, feline subjects, and canine subjects.

In at least one embodiment, treating is carried out on a solid support. Suitable solid supports include, without limitation, monolayer culture supports, three-dimensional tissue scaffolds, hydrogels, and foamed scaffolds made of resorbable biomaterials. A three-dimensional cell scaffold should possess sufficient mechanical strength to maintain its form and structure in response to the pressure exerted by the surrounding tissue upon implantation in situ and to the strain exerted on the scaffold by cells in the interior of the scaffold. The aim of the scaffold structure and cells in the interior of the scaffold or native cells of the surrounding tissue is to perform the function of the native cells or tissue that they are meant to supplement or replace. Consequently, an environment which allows for growth and differentiation of the cells of the scaffold into tissue should be provided by the three-dimensional scaffold. A number of scaffolds for implantation into a recipient are well-known (see, e.g., U.S. Patent Pub. Nos. 2004/0126405 to Sahatjian et al., 2005/0107868 to Nakayama et al., 2006/0039947 to Schmidmaier et al., and PCT Pub. No. WO/2008/003320 to Ulrich-Vinther et al., all of which are hereby incorporated by reference in their entirety). The treating may also be carried out on gel matrix, such as a hydrogel. Examples of gel matrices that may be used include, but are not limited to, collagen gel, fibrin glue, polyglycolic acid, polylactic acid, polyethylene oxide gel, alginate or calcium alginate gel, poly-(2-hydroxyethyl methacrylate) (i.e., a hydrogel), polyorthoester, hyaluronic acid, polyanhydride, chitosan, gelatin, agarose, and other bioresorbable and biocompatible materials such as those described in EP 0705878 A2 to Burns et al. and U.S. Pat. No. 8,153,117 to Binette et al., both of which are hereby incorporated by reference in their entirety. To promote chondrocyte proliferation and function, the biological gel can additionally contain appropriate nutrients (e.g., serum, salts such as calcium chloride, ascorbic acid, and amino acids) and growth factors (e.g., somatomedin, basic fibroblast growth factor, transforming growth factor-$\beta$ (as described supra), cartilage growth factor, bone-derived growth factor, or a combination thereof).

Another aspect of the present invention relates to a method of improving the phenotype of a chondrocyte population. This method includes selecting a population of chondrocytes having a poor chondrocytic phenotype and treating the selected cell population with a ceramidase to improve the chondrocytic phenotype of the population.

Suitable chondrocytes according to this aspect of the present invention include, without limitation, articular chondrocytes, nasal chondrocytes, tracheal chondrocytes, meniscal chondrocytes, and aural chondrocytes. These include, for example, mammalian chondrocytes, e.g., human chondrocytes, equine chondrocytes, porcine chondrocytes, feline chondrocytes, and canine chondrocytes. Preferably, the chondrocytes are primary chondrocytes.

The term "chondrogenic phenotype" refers to the observable characteristics at any level—physical, morphologic, biochemical, or molecular—of a chondrocyte cell or tissue. Typically, the chondrocytic phenotype is determined by evaluating one or more chondrocyte markers, i.e., a substance whose localization or expression in a chondrocyte aids in the identification of the chondrocyte. These include, for example, collagen 2A1, collagen 10, type IX collagen, type XI collagen, Sox9, aggrecan, GAPDH, TGF$\beta$1, FGF-2, cartilage proteoglycan (aglycan) or components thereof, hyaluronic acid, and chondromodulin.

In at least one embodiment, a poor chondrogenic phenotype is characterized by low expression of collagen 2A1, Sox9, and aggrecan; elevated expression of collagen 10; low staining for proteoglycans with Alcian Blue or Safranin O; and/or low expression of other chondrocyte-specific growth factors. In at least one embodiment, an improved chondrogenic phenotype is characterized by elevated expression of collagen 2A1, Sox9, and aggrecan; low expression of collagen 10; enhanced staining for proteoglycans with Alcian Blue or Safranin O; and/or elevated expression of other chondrocyte-specific growth factors.

Suitable ceramidases and methods of treating the population of cells with ceramidase include all those set forth supra.

Another aspect of the present invention relates to a method of promoting chondrogenesis. This method includes selecting a population of bone marrow cells in need of differentiation into chondrocytes, treating the population of bone marrow cells with a ceramidase to enrich mesenchymal stem cells within the bone marrow cell population, and treating the population of enriched mesenchymal stem cells with a ceramidase, or a ceramidase and TGF$\beta$, to promote differentiation of mesenchymal stem cells into chondrocytes.

Suitable bone marrow cells according to this and all other aspects of the present invention include mammalian bone marrow cells, e.g., human bone marrow cells, equine bone marrow cells, porcine bone marrow cells, feline bone marrow cells, and canine bone marrow cells. Human bone marrow cells are particularly preferred.

In at least one embodiment, the method further includes treating the chondrocytes with a ceramidase to improve the phenotype of the chondrocytes, as discussed supra.

Suitable ceramidases and methods of treating the populations of cells with ceramidase include all those set forth supra.

Another aspect of the present invention relates to a method of maintaining a cell population in a differentiated state or increasing the number of cells of a population in a differentiated state. This method includes selecting a cell population in need of being maintained in a differentiated state or a cell population in need of an increased number of cells in a differentiated state and treating the selected cell population with a ceramidase to maintain or increase the number of differentiated cells in the selected cell population.

Suitable cells populations according to this aspect of the present invention include mammalian cells populations, e.g., human cells populations, equine cells populations, porcine cells populations, feline cells populations, and/or canine cells populations. Human cells populations are particularly preferred.

In at least one embodiment, the differentiated cells are primary cells. Suitable differentiated cells include, without limitation, chondrocytes, neurons, hepatocytes, bone cells, lung cells, and cardiac cells. In a preferred embodiment, the cells are chondrocytes. Suitable chondrocytes include those described supra.

In at least one embodiment, the number of differentiated cells in the cell population is maintained. In at least one embodiment, the number of differentiated cells in the cell population is increased. As will be apparent to the skilled artisan, maintaining or increasing the overall number of differentiated cells in the population can be achieved by decreasing or preventing de-differentiation of cells in the population that are already differentiated, by stimulating the differentiation of undifferentiated cells in the population, or both.

Suitable ceramidases and methods of treating the populations of cells with ceramidase include all those set forth supra.

Another aspect of the present invention relates to a method of producing a population of differentiated cells. This method includes selecting a population of stem cells capable of differentiating into a desired population of differentiated cells, selecting a differentiation medium capable of stimulating differentiation into the desired differentiated cells, and culturing the population of stem cells in the differentiation medium and ceramidase to stimulate differentiation into the population of differentiated cells.

Suitable stem cells according to this aspect of the present invention include, without limitation, embryonic stem cells, somatic stem cells, induced pluripotent stem cells, totipotent stem cells, pluripotent stem cells, and multipotent stem cells. Exemplary stem cells include, for example, hematopoietic stem cells, mesenchymal stem cells, neural stem cells, endothelial progenitor cells, epithelial stem cells, epidermal stem cells, and cardiac stem cells.

The differentiated cells of this aspect of the present invention may be selected from, but are not limited to, red blood cells, B lymphocytes, T lymphocytes, natural killer cells, neutrophils, basophils, eosinophils, monocytes, macrophages, muscle cells, osteoblasts, osteocytes, chondrocytes, adipocytes, stromal cells, glial cells, astrocytes, oligodendrocytes, neurons, endothelial cells, absorptive cells, goblet cells, Paneth cells, enteroendocrine cells, keratinocytes, skin cells, cardiac cells, and pancreatic cells. Chondrocytes, neurons, cardiac cells, and pancreatic cells are particularly preferred. The selection of suitable stem cells and suitable differentiation media to produce the desired differentiated cells will be apparent to the skilled artisan.

Suitable ceramidases include all those set forth supra.

Culturing according to this aspect of the present invention may be carried out as described above.

In at least one embodiment, culturing is carried out in vivo, e.g., in the body of a mammalian subject. Suitable mammalian subjects include human subjects, equine subjects, porcine subjects, feline subjects, and canine subjects. The population of stem cells can be produced by the subject or, alternatively, the population of stem cells (which can be either homologous or heterologous) can be artificially introduced into the subject. The differentiation medium can be a commercial differentiation medium or a natural differentiation medium produced by the subject. In addition to the culturing methods described supra, culturing according to these embodiments can include, for example: implanting in the subject a solid support as described above (e.g., a tissue scaffold) having the ceramidase disposed thereon and/or therein, administering the ceramidase to the subject at a tissue site containing the population of stem cells, and/or selectively damaging a tissue of the subject to stimulate production of the differentiation medium.

In all embodiments that involve administering ceramidase to a subject, an active ceramidase, ceramidase precursor protein, and/or nucleic acid encoding ceramidase/ceramidase precursor protein can be administered. Administration can be accomplished either via systemic administration to the subject or via targeted administration to affected tissues, organs, and/or cells. The ceramidase may be administered to a non-targeted area along with one or more agents that facilitate migration of the ceramidase to (and/or uptake by) a targeted tissue, organ, or cell. Additionally and/or alternatively, the ceramidase itself can be modified to facilitate its transport to (and uptake by) the desired tissue, organ, or cell, as will be apparent to one of ordinary skill in the art.

Typically, ceramidase will be administered to a subject in a vehicle that delivers the ceramidase to the target cell, tissue, or organ. Exemplary routes of administration include, without limitation, by intratracheal inoculation, aspiration, airway instillation, aerosolization, nebulization, intranasal instillation, oral or nasogastric instillation, intraperitoneal injection, intravascular injection, topically, transdermally, parenterally, subcutaneously, intravenous injection, intra-arterial injection (such as via the pulmonary artery), intramuscular injection, intrapleural instillation, intraventricularly, intralesionally, by application to mucous membranes (such as that of the nose, throat, bronchial tubes, genitals, and/or anus), or implantation of a sustained release vehicle.

In some embodiments, ceramidase is administered orally, topically, intranasally, intraperitoneally, intravenously, subcutaneously, or by aerosol inhalation. In some embodiments, ceramidase is administered via aerosol inhalation. In some embodiments, ceramidase can be incorporated into pharmaceutical compositions suitable for administration, as described herein.

The ceramidase may be orally administered, for example, with an inert diluent, or with an assimilable edible carrier, or they may be enclosed in hard or soft shell capsules, or they may be compressed into tablets, or may be incorporated directly with the food of the diet. For oral therapeutic administration, ceramidase may be incorporated with excipients and used in the form of tablets, capsules, elixirs, suspensions, syrups, and the like. Such compositions and preparations should contain at least 0.1% of ceramidase. The percentage of ceramidase in these compositions may, of course, be varied and may conveniently be between about 2% to about 60% of the weight of the unit. The amount of ceramidase in such therapeutically useful compositions is such that a suitable dosage will be obtained.

The tablets, capsules, and the like may also contain a binder such as gum tragacanth, acacia, corn starch, or gelatin; excipients such as dicalcium phosphate; a disintegrating agent such as corn starch, potato starch, or alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

The ceramidase may also be administered parenterally. Solutions or suspensions of ceramidase can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

Ceramidase may also be administered directly to the airways in the form of an aerosol. For use as aerosols, ceramidase in solution or suspension may be packaged in a pressurized aerosol container together with suitable propellants, for example, hydrocarbon propellants like propane, butane, or isobutane with conventional adjuvants. Ceramidase may also be administered in a non-pressurized form.

Exemplary delivery devices include, without limitation, nebulizers, atomizers, liposomes (including both active and passive drug delivery techniques) (Wang & Huang, "pH-Sensitive Immunoliposomes Mediate Target-cell-specific Delivery and Controlled Expression of a Foreign Gene in Mouse," *Proc. Nat'l Acad. Sci. USA* 84:7851-5 (1987); Bangham et al., "Diffusion of Univalent Ions Across the Lamellae of Swollen Phospholipids," *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; and U.S. Pat. No. 5,059,421 to Loughrey et al.; Wolff et al., "The Use of Monoclonal Anti-Thy1 IgG1 for the Targeting of Liposomes to AKR-A Cells in Vitro and in Vivo," *Biochim. Biophys. Acta* 802:259-73 (1984), each of which is hereby incorporated by reference in its entirety), transdermal patches, implants, implantable or injectable protein depot compositions, and syringes. Other delivery systems which are known to those of skill in the art can also be employed to achieve the desired delivery of ceramidase to the desired organ, tissue, or cells.

Administration can be carried out as frequently as required and for a duration that is suitable to provide effective treatment. For example, administration can be carried out with a single sustained-release dosage formulation or with multiple daily doses.

The amount to be administered will, of course, vary depending upon the treatment regimen. The dose required to obtain an effective amount may vary depending on the agent, formulation, and individual to whom the agent is administered.

Typically, ceramidase will be administered as a pharmaceutical formulation that includes ceramidase and any pharmaceutically acceptable adjuvants, carriers, excipients, and/or stabilizers, and can be in solid or liquid form, such as tablets, capsules, powders, solutions, suspensions, or emulsions. The compositions preferably contain from about 0.01 to about 99 weight percent, more preferably from about 2 to about 60 weight percent, of ceramidase together with the adjuvants, carriers and/or excipients. In some embodiments, an effective amount ranges from about 0.001 mg/kg to about 500 mg/kg body weight of the subject. In some embodiments, the effective amount of the agent ranges from about 0.05 mg/kg to about 30 mg/kg, from about 0.1 mg/kg to about 30 mg/kg, from about 1 mg/kg to about 25 mg/kg, from about 1 mg/kg to about 20 mg/kg, or from about 1 or 2 mg/kg to about 15 mg/kg.

Further aspects of the present invention relate to methods of treating a certain disease or disorder. These methods involve selecting a mammalian subject having the disease or disorder and administering a population of certain cells to the subject to treat the disease or disorder.

In these aspects of the present invention, the population of cells is produced by selecting a population of stem cells capable of differentiating into a desired population of differentiated cells, selecting a differentiation medium capable of stimulating differentiation into the desired differentiated cells, and culturing the population of stem cells in the differentiation medium and ceramidase to stimulate differentiation into the population of differentiated cells, as described supra.

In at least one embodiment, culturing is carried out in vitro. In these embodiments, the population of stem cells can be taken from the subject or from a second subject before culturing, culturing carried out in vitro to produce differentiated cells, and the differentiated cells then administered to the first subject (e.g., by injecting the differentiated cells into the first subject).

In at least one embodiment, culturing is carried out in vivo. In these embodiments, the population of stem cells can be produced by the subject or by a second subject. Culturing can be carried out, for example, in the first subject or the second subject, using the in vivo culturing methods described above. In at least one embodiment, the stem cells are produced by the subject and culturing includes administering the ceramidase to the subject at a tissue site containing the population of stem cells. In at least one embodiment, the stem cells are produced by a second subject and culturing includes administering the ceramidase to the second subject at a tissue site containing the population of stem cells. Ceramidase can be administered to the first or second subject using the methods described above.

Mammalian subjects according to these aspects of the present invention include, for example, human subjects, equine subjects, porcine subjects, feline subjects, and canine subjects. Human subjects are particularly preferred.

In one aspect, the disease or disorder is a joint disease or disorder and a population of chondrocytes produced according to the methods of the present invention is administered. Exemplary types of joint disease or disorders include, without limitation, osteoarthritis, Rheumatoid arthritis, mucopolysaccharidosis, degenerative joint disease, and joint injury.

In another aspect, the disease or disorder is a neurodegenerative disease or disorder and a population of neurons produced according to the methods of the present invention is administered. Exemplary types of neurodegenerative diseases or disorders include, without limitation, Alzheimer's disease, Frontotemporal Dementia, Dementia with Lewy Bodies, Prion disease, Parkinson's disease, Huntington's disease, Progressive Supranuclear Palsy, Corticobasal Degeneration, Multiple System Atrophy, amyotrophic lateral sclerosis, inclusion body myositis, degenerative myopathy, spinocerebellar atrophy, metabolic neuropathy, diabetic neuropathy, endocrine neuropathy, orthostatic hypotension, brain injury, spinal cord injury, and stroke.

In another aspect, the disease or disorder is a cardiac disease or disorder and a population of cardiac cells produced according to the methods of the present invention is administered. Exemplary types of cardiac diseases or disorders include, without limitation, heart disease, cardiac injury, hypercardia, heart infarction, mitral regurgitation, aortic regurgitation, septal defect, and tachycardia-bradycardia syndrome.

In another aspect, the disease or disorder is diabetes and a population of pancreatic cells produced according to the method of the present invention is administered.

Any suitable approach for administering the population of cells to the subject can be utilized to practice these aspects of the present invention, as will be apparent to the skilled artisan. This may include, for example, transplantation to a particular site in the body, such as a particular tissue or organ. Systemic infusion of cells may also be performed.

Therapeutic agents to treat the disease or disorder can also be administered in addition to administering the population of cells, as will be apparent to the skilled artisan.

Dosage, toxicity, and therapeutic efficacy of therapeutic agents and/or cells can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents/cells which exhibit high therapeutic indices may be desirable. While agents/cells that exhibit toxic side effects may be used, care should be taken to design a delivery system that targets such agents/cells to the site of affected tissue in order to minimize potential damage to uninfected cells and, thereby, reduce side effects.

Therapeutic agents and/or cells are administered to a subject in an amount to treat the disease or disorder. The amount is a quantity sufficient to achieve a desired therapeutic and/or prophylactic effect, e.g., an amount which results in the prevention of, or a decrease in, the cause or symptoms associated with the disease or disorder that is being treated.

The effective amount of a therapeutic agent/cell population of the present invention administered to the subject will depend on the type and severity of the disease or disorder and on the characteristics of the individual, such as general health, age, sex, body weight, and tolerance to drugs. It will also depend on the degree, severity, and type of disease or disorder. The skilled artisan will be able to determine appropriate dosages depending on these and other factors.

It is to be appreciated that certain aspects, modes, embodiments, variations and features of the present invention are described in various levels of detail in order to provide a substantial understanding of the present technology. The definitions of certain terms as used in this specification are also provided. Unless defined otherwise, all technical and scientific terms used herein generally have the same meaning as commonly understood by one of ordinary skill in the art to which this invention belongs.

EXAMPLES

The following examples are provided to illustrate embodiments of the present invention but are by no means intended to limit its scope.

Example 1—Materials and Methods

Animals—

Animals were raised under National Institutes of Health and USDA guidelines for the care and use of animals in research. Normal rats were derived from the MPS VI breeding colony (Kunieda et al., "Mucopolysaccharidosis Type VI in Rats: Isolation of cDNAs Encoding Arylsulfatase B, Chromosomal Localization of the Gene, and Identification of the Mutation," *Genomics* 29(3):582-7 (1995), which is hereby incorporated by reference in its entirety) maintained at the Mount Sinai School of Medicine, while the larger animals (cats and horses) were maintained at the University of Pennsylvania School of Veterinary Medicine. The animals were housed with ad libitum food and water. Euthanasia was performed on cats using 80 mg/kg of sodium pentobarbital (Veterinary Laboratories, Lenexa, Kans.) in accordance with the American Veterinary Medical Association guidelines. Euthanasia of rats was performed using carbon dioxide inhalation. Equine cells were obtained during routine surgical procedures.

Primary Chondrocyte Isolation and Culture—

Methods for rat articular chondrocyte isolation and culture have been published elsewhere (Simonaro et al., "Mechanism of Glycosaminoglycan-mediated Joint and Bone Disease: Implications for the Mucopolysaccharodoses and Other Connective Tissue Diseases," *Am. J. Path.* 172: 112-122 (2008), which is hereby incorporated by reference in its entirety). Briefly, to establish rat primary chondrocyte cultures, femoral caps and meniscus were collected and washed three times in 0.9% NaCl supplemented with 5% penicillin/streptomycin (v/v) and fungizone 0.1% (v/v). The cartilage was digested with 0.5 mg/ml pronase prepared in 0.9% NaCl (v/v)+5% penicillin/streptomycin (v/v)+0.1% fungizone for 2 hours at 37° C., and with 1 mg/ml collagenase (Sigma Chemical Co.) prepared in DMEM containing 10% FBS (v/v), 1% penicillin/streptomycin (v/v), and 0.1% fungizone overnight at 37° C. Cells were then cleaned by filtrating the resulting media through a 40 lam cell strainer, and isolated by centrifugation (1200 rpm for 8 minutes). They were further washed twice in DMEM supplemented with 10% FBS (v/v), 1% Pen Strep (v/v), and fungizone 0.1%, and plated in 75 cm$^2$ flasks at a density of 7000 cells per cm$^2$ in DMEM containing 10% FBS (v/v), 1% penicillin/streptomycin (v/v), and fungizone 0.1%. The freshly plated cells were considered passage 0 (P0). When reaching subconfluency, cells were trypsinized and passaged (P1) for further expansion. For subsequent passages, the cells were grown for seven days, trypsinized, and then re-seeded at the same cell density. In some experiments rAC was added to the media at P0 (200 U/ml final concentration). Unless otherwise noted, rAC was added to the cells only once, and subsequent media changes did not include the enzyme.

To grow rat chondrocytes in three-dimensional cultures, 5×5 mm collagen sponges (CollaCote, Zimmer Dental) were used. The sponges were pre-wet in DMEM containing 10% FBS (v/v) and antibiotics, and the cells, which had been previously isolated as described above, were suspended in media and pipetted onto the sponge. To distribute the chondrocytes throughout the sponge, it was compressed slightly to circulate the media and distribute the cells. The sponges were then placed in culture dishes and grown in DMEM containing 10% FBS and antibiotics with and without rAC. The media was changed every three days with fresh media lacking rAC.

To grow rat chondrocytes in fibrin gels, $7.5 \times 10^6$ cells were seeded in 200 µl of TISSEEL® (Baxter Healthcare, Deerfield, Ill.) gel in 96 well plates and cultured in standard media (DMEM containing 10% FBS) with or without rAC (200 U/ml). Media was changed every four days with fresh rAC included each media change. Cells were maintained for two weeks prior to analysis.

To obtain equine articular chondroytes, cartilage explant tissue was recovered from the articular surfaces of the stifle joints of geldings (age 3-12 years) by use of a 6-mm biopsy punch. The punch was pushed into the cartilage perpendicular to the articular surface until contact was made with the surface of the bone. The punch was then rotated and removed and the resultant explant was removed from the bone by use of a scalpel blade via dissection parallel to the articular surface. Cartilage explants were trimmed to a thickness of approximately 100 mm to eliminate any mineralized tissue that might have affected subsequent culture or analysis procedures. Chondrocytes were isolated from explant tissue as described elsewhere (Novotny et al., "Biomechanical and Magnetic Resonance Characteristics of a Cartilage-like Equivalent Generated in a Suspension Culture," *Tissue Eng* 12:2755-2764 (2006), which is hereby incorporated by reference in its entirety), and either frozen (P0) or used for cell expansion in DMEM/F12 media containing 50 µg of ascorbate-2-phosphate/ml (v/v), 1% (v/v) penicillin/streptomycin, 1% (v/v) glutamate, and 0.1% (v/v) fungizone.

Human articular cartilage was collected from patients undergoing total knee replacement surgery with written consent in accordance with an IRB-approved protocol (#09-0248). Cartilage slices were collected into DMEM/F12 media without FBS (containing 1% (v/v) penicillin/streptomycin, 1% (v/v) glutamate, and 0.1% (v/v) fungizone), and then incubated with Pronase (1 mg/ml) in DMEM/F12 containing 10% FBS (v/v) for 30 minutes at 37° C. in a shaker. Following centrifugation at 200×g, the cartilage was washed twice with PBS and then incubated with collagenase P (1 mg/ml) in DMEM/F12 containing 10% FBS (v/v) overnight at 37° C. in a shaker. The cartilage was then filtered using a 40-70 µm filter, centrifuged, and the supernatant was discarded. The cells were washed once with PBS, resuspended in DMEM/F12 media containing 10% FBS (v/v), and then plated at a density of $1 \times 10^5/cm^2$. In some experiments, rAC was added to the culture media immediately at the time of cell plating (200 U/ml final concentration).

Acid Ceramidase, Ceramide, and Sphingosine Measurements—

Rat chondrocytes were grown in 12-well plates with or without rAC (200 U/ml), and AC activity, ceramide, and sphingosine levels were determined in cell lysates at 12, 24, and 48 hours. Cells were harvested and total proteins were extracted using Cell Lytic™M Cell Lysis Reagent (Sigma, Saint Louis, Mo., USA). Proteins were quantified (Bio-Rad, Hercules, Calif., USA), and the lysates were subjected to AC enzymatic activity measurement (He et al., "A Fluorescence-based High-performance Liquid Chromatographic Assay to Determine Acid Ceramidase Activity," *Anal. Biochem.* 274 (2):264-9 (1999), which is hereby incorporated by reference in its entirety). Lipids also were extracted from the cell lysates, and ceramide and sphingosine levels were quantified as already published (He et al., "Deregulation of Sphingolipid Metabolism in Alzheimer's Disease," *Neurobiol. Aging* 31(3):398-408 (2010), which is hereby incorporated by reference in its entirety).

Mesenchymal Stem Cell Isolation and Culture—

Rat MSCs were obtained from the femoral and tibia cavities of adult rats. Femurs and tibias were isolated, the extremities were removed, and the bone marrow was flushed out using PBS. After two washings in PBS, bone marrow cells were counted and plated at a density of $5 \times 10^6$ cells/cm$^2$ in Alpha MEM supplemented with 20% (v/v) FBS, 1% (v/v) penicillin/streptomycin, 1% (v/v) glutamate, and 0.1% (v/v) fungizone. Bone marrow cells from cats were collected during surgical procedures and shipped on ice and in PBS overnight.

For horses, bone marrow was collected aseptically from the sternum by use of an 11-gauge bone marrow biopsy needle and a 60-ml sterile Luer-tip syringe that contained 10 ml of sterile acid-citrate-dextrose solution. After aspiration of the bone marrow, the aspirate was briefly mixed with the acid-citrate-dextrose solution, and the syringe then was placed on ice and transported to the laboratory for isolation of MSCs. Once received, cells were washed twice with PBS and plated at a density between $1-5 \times 10^6$ cells/cm$^2$ (feline cells) and $3 \times 10^8$ cells/cm$^2$ (equine cells) in Alpha MEM supplemented with 20% (v/v) FBS, 1% (v/v) penicillin/streptomycin, 1% (v/v) glutamate, and 0.1% (v/v) fungizone. The freshly plated bone marrow cells were treated with or without rAC at day 0 (200 U/ml final concentration). At day three, medium was removed and replaced by fresh medium lacking rAC. Medium was subsequently changed twice a week, and colonies were passaged when they reached subconfluency.

In some experiments, the cells were stained after one week of culture with crystal violet (0.5% [Sigma] w/v in methanol) to count the number of colonies. For these assays (CFU-F), cells were incubated 30 minutes at room temperature and rinsed four times with PBS, before a final washing in water. Only colonies with a diameter greater than 1 mm were counted.

In other experiments, flow cytometric analysis was performed to assess the number of MSCs. For these analyses, MSCs were collected, washed twice in PBS supplemented with 2% FBS and marked for CD90-FITC and CD45-PE (Cat#11-0900-81 and Cat#554878, respectively, BD Biosciences Pharmingen, San Diego, Calif., USA), diluted in PBS+FBS 2% for 15 minutes, on ice and in the dark. After subsequent washings, cells were analyzed in a LSR II flow cytometer (BD Biosciences, San Jose, Calif., USA). Flow cytometry analysis could not be performed on the cat and horse cells due to the lack of suitable antibody reagents.

To test the effect of rAC on the chondrogenic potential of BM-MSCs, bone marrow cells were amplified for 3 weeks in Alpha MEM supplemented with 20% (v/v) FBS, 1% (v/v) penicillin/streptomycin, 1% (v/v) glutamate, and 0.1% (v/v) fungizone. During the three weeks of culture, the cells were passaged when they reached subconfluency. At the end of three weeks they were trypsinized, counted, and $5 \times 10^5$ cells were differentiated in pellet cultures using conical culture tubes. Chondrogenic differentiation was performed in DMEM high glucose media containing 6.25 µg/ml insulin, 6.25 µg/ml transferin, 1.25 mg/ml bovine serum albumin, dexamethasone 100 nM, ascorbate-2-phosphate 50 µM, 5.33 µg/ml linoleic acid, and 10 ng/ml TGFβ1, as described previously (Anjos-Afonso et al., "Isolation, Culture and Differentiation Potential of Mouse Marrow Stromal Cells," CURR. PROTOC. STEM CELL BIOL. Chapter 2, Unite 2B.3 (2008), which is hereby incorporated by reference in its entirety). To evaluate the effect of rAC on the chondrogenic differentiation, in some experiments rAC was added into the chondrogenic medium (200 U/ml final concentration). Medium was changed every three days, with or without rAC. Cells were maintained in a humidified incubator, at 37° C. under 5% $CO_2$.

Recombinant AC Production and Purification—

Human recombinant AC (rAC) was produced as described in He et al., "Purification and Characterization of Recombinant, Human Acid Ceramidase. Catalytic Reactions and Interactions With Acid Sphingomyelinase," *J. Biol. Chem.* 278(35):32978-86 (2003), which is hereby incorporated by reference in its entirety. Briefly, rAC overexpressing CHO cells were grown to confluency in DMEM supplemented with 10% v/v FBS and 1% penicillin/streptomycin. The conditioned medium was collected, and rAC was concentrated by pressure filtration (cut off 30 kDa, Amicon, Billerica, Mass., USA) and purified using a fast protein liquid chromatography (FPLC) system (Amersham Biosciences, Piscataway, N.J., USA). The amount of rAC was quantified by enzyme activity measurement and western blot analysis (Eliyahu et al., "Acid Ceramidase is a Novel Factor Required for Early Embryo Survival," *FASEB J.* 21(7): 1403-9 (2007), which is hereby incorporated by reference in its entirety).

Processing of the Differentiated Mesenchymal Stem Cell Pellet Cultures—

Once BM-MSCs were differentiated in the chondrogenic media with or without rAC, pellets were removed from the incubator, washed twice, and fixed in paraformaldehyde 4% for 15 minutes at room temperature. They were then dehydrated by successive incubations in 70% ethanol (30 minutes at room temperature), 95% ethanol (2×30 minutes at room temperature), and 100% ethanol (2×30 minutes at room temperature). Pellets were then cleared in two successive baths of xylenes (2×30 minutes at room temperature), and paraffin embedded and microtome processed to create 6 µm slices on polyprep slides (Sigma).

For histochemical staining, pellets were deparaffinized in xylenes, hydrated to distilled water, and stained with either Alcian Blue 8GX 1% (w/v), pH 2.5 (Sigma) for 30 minutes at room temperature or Safranin O (Sigma) 0.1% (w/v) for 5 minutes at room temperature. Slides were washed, dehydrated, and cleared with xylenes before covering with mounting medium.

Immunohistochemistry—

For immunohistochemical analysis, pellets were deparaffinized in xylenes, hydrated, and washed three times in PBS. If needed (i.e. for Sox9 immunostaining), cells were permeabilized in 0.2% (v/v) Triton X-100 made in PBS (pH 7.4) for five minutes at room temperature, post-fixed in paraformaldehyde, and washed in PBS several times. Slides were then blocked two hours at room temperature in PBS supplemented with tween 0.1% (v/v) and 10% (v/v) FBS. After blocking, slides were incubated with primary antibody diluted in PBS containing 0.1% Tween 0.1 and 5% FBS overnight at 4° C. The following primary antibodies from Santa Cruz Biotechnology, Santa Cruz, Calif., were used for immunostaining: Rabbit anti-Sox 9 (H-90, sc-20095), rabbit anti-collagen IIA1 (H-300, sc-28887), goat anti-collagen XA1 (E-14, sc-323750), and goat anti-aggrecan (D-20, sc-16492). After exposure to the primary antibodies, slides were then incubated one hour at room temperature with the corresponding secondary antibody conjugated with Cy3, diluted in PBS/tween 0.1%/10% FBS. Finally, the slides were washed several times in PBS, and mounted with a DAPI containing medium (Vector Laboratories, Burlingame, Calif., USA). Localization of the primary antibodies was visualized using the fluorescent Cy-3 second antibody and laser-scanning confocal microscopy (Zeiss LSM510).

For immunohistochemistry of the primary chondrocyte cultures, P3 cells were plated on chamber slides (5000 cells/chamber, lab-tek2 chamber slide, Thermo Fisher Scientific) and grown until subconfluency. Cells were then washed twice in PBS, and fixed in paraformaldehyde 4% for 15 minutes at room temperature, and immunostained as described above.

Western Blot Analysis—

Primary chondrocytes were harvested by trypsinization and washed, and the proteins were extracted in Cell Lytic™ M Cell Lysis Reagent (Sigma, Saint Louis, Mo., USA). Proteins were quantified (Bio-Rad, Hercules, Calif., USA) and analyzed by western blotting (Novex Protein Analysis Solutions, Invitrogen, Carlsbad, Calif., USA). The following primary antibodies were used for western blot analysis from Santa Cruz Biotechnology, CA, USA. Rabbit anti-Sox 9 (H-90, sc-20095), goat anti-collagen 1A2 (M-19, sc-8788), rabbit anti-collagen 2A1 (H-300, sc-28887), goat anti-aggrecan (D-20, sc-16492), mouse anti-FGF2 (sc-135905), rabbit anti TGFβ1 (sc146), mouse anti-Bax (2D2) (sc-20067), rabbit anti-PARP-1/2 (H-250) (sc-7150), rabbit anti-GAPDH (FL-335) (sc-25778), and goat anti-actin (C-11) (sc-1616). Rabbit anti-collagen X (ab58632) from Abcam (Cambridge, Mass., USA) was also used.

RNA Isolation and Quantitative RT-PCR—

For RNA isolation, cells were trypsinized, washed twice in PBS, and resuspended in Trizol/chloroform (5/1 (v/v)) (Life Technologies). After centrifugation, the aqueous upper phase was saved and purified through an affinity column (RNeasy Mini Kit, Qiagen, Valencia, Calif., USA) according to the manufacturer's instructions. RNA was resuspended in RNase-free water and quantified, and 1 µg of RNA was subjected to reverse transcription.

For qPCR analysis of the human articular chondrocyte cultures, cDNA was synthesized with Superscript VILO (Invitrogen). SYBR green qPCR (Invitrogen Platinum Taq) was performed and gene expression was normalized to GAPDH ($2^\wedge$-ddCt method).

Statistical Analysis—

Where appropriate, statistical analysis was carried out using a standard student's t-test analysis, one-way analysis of variance (ANOVA) with the variable group, multivariate analyses of variance (MANOVAs) followed by post hoc Bonferroni adjustments. The results were considered significant at $P<0.05$. Statistics were performed using Sigma Stat 3.1 (Systat Software).

Example 2—Changes in Sphingolipid Metabolism Following rAC Treatment of Primary Articular Chondrocytes Primary rat articular chondrocytes were isolated and grown in monolayer cultures as described in Example 1 using DMEM containing 10% FBS with or without rAC. For the baseline timepoint, cells were collected from 6 rats and pooled without culture. The acid ceramidase, ceramide, and sphingsoine levels in these cell lysates were compared to cells grown for 12, 24, and 48 hours with or without rAC. The data is summarized in FIGS. 1A-1C.

As expected, cells grown in media supplemented with rAC exhibited markedly increased AC activity by 12 hours, and this was sustained through 48 hours. Ceramide levels were also increased compared to baseline by 12 hours, but less in cells exposed to rAC. In fact, by 48 hours the ceramide levels in the rAC-treated cells had returned to baseline, while in those without rAC treatment remained significantly elevated. Also, by 48 hours significant elevations of sphingosine, the product of AC activity, was increased in the rAC-treated cells. By 7 days AC, ceramide, and sphingosine levels had returned to baseline regardless of rAC treatment.

Overall, these results demonstrated that rAC was taken up by rat chondrocytes and retained biological activity by hydrolyzing ceramide and producing sphingosine. The fact that the AC levels were returned to baseline by 7 days was consistent with its expected intracellular half-life of 48-72 hours (Bernardo et al., "Purification, Characterization and Biosynthesis of Human Acid Ceramidase," *J. Biol. Chem.* 270(19):11098-102 (1995), which is hereby incorporated by reference in its entirety).

Example 3—Effects of rAC Supplementation on Expanded Monolayer Cultures of Primary Articular Chondrocytes The effects of rAC supplementation on the phenotype of articular chondrocytes after cell expansion were next evaluated. For these experiments, rat chondrocytes were grown for three weeks with and without rAC in DMEM containing 10% FBS. rAC was added once at the time of the initial cell plating (P0). All analyses were performed at the end of the three-week expansion period unless otherwise mentioned.

No effect of rAC treatment on the total number of cells was observed (FIG. 2A), consistent with the fact that the levels of two apoptotic markers, Bax and PARP, were also very similar with and without rAC treatment.

However, despite obtaining the same number of cells, there was a marked effect of rAC treatment on cell quality at the end of the 3-week expansion period, as determined by the expression of various chondrocyte markers. As shown in FIG. 2B, western blot analysis revealed that the expression of collagen 2A1, collagen IA2, Aggregan, Sox9, TGFβ1, and FGF2 each was enhanced in cells treated with rAC. Similar effects were evident in cells grown using a different culture media, RPMI containing 10% FBS. Notably, expression of collagen X, a marker of chondrocyte hypertrophy and de-differentiation (Nadzir et al., "Comprehension of Terminal Differentiation and Dedifferentiation of Chondrocytes During Passage Cultures," *J. Biosci. Bioeng.* 112(4): 395-401 (2011), which is hereby incorporated by reference in its entirety), was reduced in these cultures.

In order to confirm that the effects of rAC were not rat-specific, equine articular chondrocytes that were provided frozen at P0 were next studied. The frozen cells were thawed and expanded for three weeks without rAC, and then re-plated with or without rAC in the culture media. They were then grown for one additional week and then analyzed. As shown in FIG. 2C, the expression of three important chondrocyte markers, aggregan, Sox9, and collagen II, were markedly enhanced in the rAC-treated cells, consistent with what was observed in the rat. The lack of other equine-specific antibodies precluded the analysis of additional chondrocyte markers in these cultures. Of interest, a reduction in the expression of the pro-apoptotic Bax protein in the rAC-treated equine cells was observed, more than that seen in the rat cells. This could be due to the fact that the equine cells were provided to researchers frozen, eliciting additional stress-related cell death during the culture period that was reduced by rAC.

Next, the rAC-treated and untreated rat chondrocytes were evaluated by immunohistochemistry and confocal microscopy. These analyses confirmed that after three week expansion the number of cells expressing collagen 2A1 in these cultures was increased approximately 40% following rAC treatment (FIG. 3A). In addition, the intracellular distribution of Sox9 appeared different, with more of the transcription factor localizing to the nucleus in the cells after exposure to rAC (FIG. 3B).

Osteoarthritis (OA) is a common, age-related disorder that results in cartilage degradation, and patients with OA frequently undergo surgical procedures to repair their defective joints. Articular cartilage was obtained from two aged OA patients and the cells expanded in monolayer culture for three weeks with or without rAC in the media (added once at the initial cell plating). In FIG. 4A, PCR analysis showed that cells from patient 1 exhibited significantly elevated expression of Sox9, collagen 2A1, aggrecan, and TNFβ1 mRNA in response to treatment. In cells from patient 2 (FIG. 4B), Sox9 expression was significantly elevated, and there was a trend towards elevated collagen IIA1 and aggrecan expression as well. As was observed with the rat and horse cells, the total number of chondrocytes obtained after the expansion period was similar, despite this differential gene expression pattern. It is again notable that no elevation of collagen X expression was observed in the rAC treated cells from either patient.

Overall, these results indicate that supplementing chondrocyte media with rAC once at the time of initial cell plating had a significant, positive effect on the chondrogenic phenotype after three weeks of expansion.

Example 4—Effects of rAC Supplementation on Three-Dimensional Culture of Primary Articular Chondrocytes To achieve effective implantation of expanded chondrocytes in patients, after the initial monolayer expansion period the cells are generally seeded onto three-dimensional scaffolds for subsequent growth and transplantation. Therefore, the effects of rAC treatment on primary rat chondrocytes grown on collagen-coated scaffolds were evaluated (FIG. 5A). For this experiment, the cells were seeded directly onto the scaffolds bathed in DMEM containing 10% FBS serum with or without rAC. They were then grown for 7 or 14 days and analyzed. As show in the representative images, cells grown in the presence of rAC were larger and maintained a rounder phenotype than those without rAC. Importantly, these cells also stained positive for Safranin O, a commonly used marker of proteoglycan expression. The degree of cell shrinkage was further quantified and significantly less shrinkage was observed in rAC treated cells (FIG. 5B).

In addition to collagen-coated scaffolds, biodegradable fibrin gels are also frequently used for implantation of the cells into the damaged cartilage site. As shown in FIG. 5C, rAC treatment of rat chondrocytes grown in such gels for two weeks exhibited enhanced staining for Alcian Blue, an important marker of proteoglycan deposition.

Example 5—Effects of rAC Supplementation on the Yield of Bone Marrow-Derived Mesencymal Stem Cells As noted above, recent interest in cell-based cartilage repair has focused on the use of MSCs, which can be readily obtained from adult bone marrow, adipose tissue, or other autologous sources, and may be induced in vitro or in vivo to form chondrocytes and other mesenchymal cell lineages.

Therefore, the effects of rAC on adult rat bone marrow-derived MSC before and after their differentiation into chondrocytes was next evaluated. Addition of rAC to the culture media at the time of initial plating of the rat bone marrow cells led to an approximate two to three-fold increase in the number of MSCs obtained at day 5, as judged by the number of colony forming fibroblast units (CFU-F) or by flow cytometry (FIG. 6A). To confirm that these findings were not rat-specific, the effect of rAC supplementation on bone marrow MSCs obtained from cats and horses was also analyzed (FIGS. 6B, 6C, 6D). Due to the lack of suitable antibody reagents for flow cytometry, the number of MSCs in these species were quantified by CFU-F only, revealing increases similar to those observed with the rat cells.

Example 6—Effects of rAC Supplementation on the Chondrogenic Differentiation of Bone Marrow Mesencymal Stem Cells The effects of including rAC on the chondrogenic differentiation media of MSCs was also evaluated. For these studies differentiation was carried out in high-density pellet cultures using standard media with or without TGFβ1 (see Example 1, supra). Rat bone marrow cells were grown for three weeks in the absence of rAC to obtain a population of adherent MSCs that was approximately 90% pure (CD90+/CD40−). They were then grown in high-density pellet cultures for an additional three weeks in chondrocyte differentiation media. As shown in FIG. 7A, rat pellets grown in the presence of rAC were significantly larger (>2-fold) and stained more intensely for proteoglycans using Alcian Blue and Safranin O. The effects of rAC were independent of TGFβ1, and the two factors worked synergistically to yield optimal results. The rat pellets also were analyzed by immunohistochemistry and confocal microscopy for Sox9, aggrecan, and collagen II expression. As illustrated by the images in FIGS. 7B-7D, the expression of these three chondrogenic markers were significantly elevated in cells supplemented with rAC. To confirm these findings, the same studies were performed using equine cells, and essentially the same results were obtained (FIGS. 8A-8D).

As described earlier for the chondrocyte expansion studies, no change or a reduction was observed in the levels of collagen X, a marker of chondrocyte hypertrophy and de-differentiation, in contrast to collagen II, which was elevated. To examine this further, the differentiated equine chondrocytes for collagen X were also stained, and it was found that the levels were decreased in cells treated with rAC (FIG. 8E). Taken together, the elevated expression of collagen II, aggrecan, and Sox9 along with low collagen X expression suggests that the treated cells have a more chondrogenic phenotype conducive to cartilage repair.

Example 7—Discussion of Examples 1-9

The dedifferentiation of chondrocytes remains one of the main barriers in ACI (Schulze-Tanzil, G., "Activation and Dedifferentiation of Chondrocytes: Implications in Cartilage Injury and Repair," *Ann. Anat.* 191(4):325-38 (2009), which is hereby incorporated by reference in its entirety). Indeed, chondrocytes, responsible for the production of a highly abundant extracellular matrix, are very sensitive to mechanical and biochemical stresses. During the amplification process it takes only a few days for the cells to change their shape from rounded to fibroblastic, and to start displaying abnormal features. For example, the cytoskeleton becomes abnormal with the expression of F-actin stress-fibers, the extracellular matrix proteins are abnormally expressed (e.g., decrease of Col 2A, proteoglycans, glycoprotein), proteases (e.g., MMPs, ADAM-TS) are activated, and signaling proteins are abnormally expressed (loss of Sox9). Moreover, although dedifferentiated cells can be re-differentiated when implanted in three-dimensional culture systems such as alginate, agarose, or fibrin systems, irreversible de-differentiation is usually observed in preparations of primary chondrocytes. Hence it is of primary interest to maintain primary chondrocytes as close as possible to their initial chondrogenic profile and/or to improve their capacity to re-differentiate prior to re-implantation.

This invention shows that a single treatment of primary chondrocytes with rAC, although not improving the yield of primary chondrocytes, greatly improves their chondrogenic phenotype after 2-3 week expansion. In particular, the expression of collagen 2A1, aggrecan, FGF2, and Sox9 was markedly increased in rat cells at the end of the 3-week expansion period (FIGS. 2A-2B and 3A-3B). In equine and human cells, the expression of these chondrogenic markers was similarly increased (FIGS. 2A-2C and 4A-4B). This improvement of the phenotype may be explained by the better subcellular localization of the transcription factor Sox9 in the nucleus of cells treated with rAC (FIG. 3A-3B), although how a single treatment with rAC influences the nuclear localization of Sox9 over several weeks remains yet unclear. Finally, when grown in three-dimensional culture systems, i.e. collagen sponges or fibrin gels, addition of rAC improved the differentiation of the cells, as shown by H&E and safranin O staining (FIGS. 5A-5C). Cells were bigger, and the better differentiation was more and more evident with time (FIGS. 5A and 5B). In addition, the expression of proteoglycans was improved in cells treated with rAC (FIG. 5C). Overall, the present Examples demonstrate that a single treatment with rAC improves the phenotype of primary chondrocytes after expansion. It is speculated that these changes are due to the short-term changes in sphingolipid metabolism induced by rAC (FIGS. 1A-1C), presumably leading to transcriptional and post-translational changes resulting in these downstream effects.

The main limitations in the use of MSCs for cell-based cartilage repair are that (i) MSCs lose their ability to differentiate into chondrocytes very early (3 or 4 passages), shortening the time for amplification prior to differentiation, and that (ii) proper ex vivo and in vivo protocols to differentiate MSCs into chondrocytes that are fully functional and do not undergo hypertrophy are still lacking Numerous articles have been published describing the use of new agents for the differentiation of MSCs toward chondrocytes. Among the candidates, proteins of the TGFβ family (TGFβ1, TGFβ3), but also bone morphogenic proteins (BMPs), are the most described. Another strategy relies on the engineering of three-dimensional scaffolds releasing growth factors, anti-apoptotic factors, or differentiation factors, in which the MSCs can be seeded at high density to mimic the natural conditions of differentiation.

In the present Examples, it is shown that (i) a single addition of rAC into the culture media of rat bone marrow increases the yield of MSCs at one week (FIGS. 6A-6D), as seen by CFU-F assay and flow cytometry analyses, and (ii) repeated treatment with rAC during the chondrogenic differentiation process improves the quality of the resulting MSC-derived chondrocytes, as seen by alcian blue staining, safranin O staining, and immunostaining (FIGS. 7A-7D and 8A-8E). Notably, the levels of Sox9, collagen IIA1, and aggrecan were more elevated in cells differentiated in the presence of rAC, but the level of collagen X was also diminished, revealing a partial blockage of hypertrophy in cells differentiated in presence of rAC.

Thus, two positive influences of rAC treatment were observed with MSCs, although the mechanisms behind these observations might be different. For example, while the treatment at P0 was probably beneficial because the rAC was reducing the stress response induced by the extraction of the cells from their natural environment and their plating in an artificial medium (yielding more viable cells), the benefit of the treatment during the differentiation process may be due to (i) rearrangement of the lipid raft structures at the cell surface and better signaling through the TGFβ pathway, (ii) a decrease in ceramide and an increase of sphingosine or S1P, known to play a role in chondrogenesis and cartilage homeostasis, and/or (iii) reduction of the stress response by itself, in particular since the differentiation medium is devoid of serum and hence a very potent stress inducer.

Overall, the present Examples for the first time show that the addition of rAC to culture media has a positive influence on the chondrogenic phenotype of expanded primary and MSC-derived chondrocytes, likely through alterations of the sphingolipid signaling pathway. These findings could have an important impact on cell-based cartilage repair by providing higher quality cells for transplantation, and/or by including the enzyme directly in three-dimensional scaffolds to improve chondrogensis in vivo.

What is claimed:

1. An in vitro method of producing chondrocytes, said method comprising:
    selecting a population of mammalian cells having the potential to differentiate into chondrocytes, and
    treating the selected cell population with a ceramidase in a differentiation medium capable of stimulating differentiation into chondrocytes to transform one or more of the cells in the selected population into chondrocytes in increased number as compared to the differentiation medium alone.

2. The method according to claim 1, wherein the cells are human cells.

3. The method according to claim 1, wherein the selected cell population comprises a population of mesenchymal stem cells and/or fibroblasts.

4. The method according to claim 3, wherein the cells are human cells.

5. The method according to claim 3, wherein the selected cell population comprises mesenchymal stem cells.

6. The method according to claim 5, wherein the selected cell population consists essentially of mesenchymal stem cells.

7. The method according to claim 5, wherein the differentiation medium comprises TGFβ.

8. The method according to claim 3, wherein the selected cell population comprises fibroblasts.

9. The method according to claim 8, wherein the selected cell population consists essentially of fibroblasts.

10. The method according to claim 1, wherein the differentiation medium comprises TGFβ.

11. The method according to claim 5, wherein the mesenchymal stem cells are derived from bone marrow.

* * * * *